(12) United States Patent
Kobayashi et al.

(10) Patent No.: US 7,001,329 B2
(45) Date of Patent: Feb. 21, 2006

(54) CAPSULE ENDOSCOPE GUIDANCE SYSTEM, CAPSULE ENDOSCOPE HOLDER, AND CAPSULE ENDOSCOPE

(75) Inventors: Hiroyuki Kobayashi, Saitama (JP); Tetsuya Tarumoto, Tokyo (JP)

(73) Assignee: PENTAX Corporation, Tokyo (JP)

( * ) Notice: Subject to any disclaimer, the term of this patent is extended or adjusted under 35 U.S.C. 154(b) by 0 days.

(21) Appl. No.: 10/623,643

(22) Filed: Jul. 22, 2003

(65) Prior Publication Data

US 2004/0133076 A1 Jul. 8, 2004

(30) Foreign Application Priority Data

Jul. 23, 2002 (JP) ............................. 2002-214494
Jul. 23, 2002 (JP) ............................. 2002-214495
Jul. 23, 2002 (JP) ............................. 2002-214514

(51) Int. Cl.
*A61B 1/00* (2006.01)

(52) U.S. Cl. .................... 600/114; 600/109; 600/118
(58) Field of Classification Search .............. 600/109, 600/114, 104, 106, 107, 117, 118, 160
See application file for complete search history.

(56) References Cited

U.S. PATENT DOCUMENTS

| | | |
|---|---|---|
| 3,465,103 A | 9/1969 | Lynch |
| 3,572,316 A | 3/1971 | Vogelman et al. |
| 3,682,160 A | 8/1972 | Murata |
| 3,683,389 A | 8/1972 | Hollis |
| 3,933,612 A | 1/1976 | Fischer et al. |
| 3,971,362 A | 7/1976 | Popo et al. |
| 4,027,510 A | 6/1977 | Hitebrandt |
| 4,090,176 A | 5/1978 | Rodler |
| 4,177,800 A | 12/1979 | Enger |
| 4,198,960 A | 4/1980 | Utsugi |
| 4,217,045 A | 8/1980 | Ziskind |
| 4,262,632 A | 4/1981 | Hanton et al. |
| 4,278,077 A | 7/1981 | Mizumoto |
| 4,439,197 A | 3/1984 | Honda et al. |
| 4,491,865 A | 1/1985 | Danna et al. |
| 4,646,724 A | 3/1987 | Sato et al. |
| 4,679,560 A | 7/1987 | Galbraith |
| 4,689,621 A | 8/1987 | Kleinberg |
| 4,741,327 A | 5/1988 | Yabe |
| 4,844,076 A | 7/1989 | Lesho et al. |
| 4,917,097 A | 4/1990 | Proudian et al. |
| 4,936,823 A | 6/1990 | Colvin et al. |
| 4,951,135 A | 8/1990 | Sasagawa et al. |

(Continued)

FOREIGN PATENT DOCUMENTS

DE     2606069     9/1976

(Continued)

OTHER PUBLICATIONS

"Diagnostic Imaging in 3 Easy Steps," date unknown.

(Continued)

*Primary Examiner*—Beverly M. Flanagan
(74) *Attorney, Agent, or Firm*—Greenblum & Bernstein, P.L.C.

(57) ABSTRACT

A capsule endoscope guidance system including a member having an elongated flexible portion which can be guided to a desired position in a body cavity of a patient's body by manipulating a distal end portion of the member wherein the elongated flexible portion bends in accordance with an operation at a proximal end portion of the member, includes a capsule endoscope holding device, provided at a distal end of the elongated flexible portion, for removably holding a capsule endoscope; and a removal/attachment manipulation device provided on the proximal end portion, for manipulating removal and attachment of the capsule endoscope holding device.

28 Claims, 13 Drawing Sheets

U.S. PATENT DOCUMENTS

| | | | |
|---|---|---|---|
| 5,010,412 | A | 4/1991 | Garriss |
| 5,042,486 | A | 8/1991 | Pfeiler et al. |
| 5,099,845 | A | 3/1992 | Besz et al. |
| 5,166,787 | A | 11/1992 | Irion |
| 5,167,626 | A | 12/1992 | Casper et al. |
| 5,170,801 | A | 12/1992 | Casper et al. |
| 5,187,572 | A | 2/1993 | Nakamura et al. |
| 5,217,449 | A | 6/1993 | Yuda et al. |
| 5,222,477 | A | 6/1993 | Lia |
| 5,241,961 | A | 9/1993 | Henry |
| 5,253,647 | A | 10/1993 | Takahashi et al. |
| 5,267,033 | A | 11/1993 | Hoshino |
| 5,273,025 | A | 12/1993 | Sakiyama et al. |
| 5,279,607 | A | 1/1994 | Schentag et al. |
| 5,316,015 | A | 5/1994 | Sinaiko |
| 5,335,662 | A | 8/1994 | Kimura et al. |
| 5,358,514 | A | 10/1994 | Schulman et al. |
| 5,368,027 | A | 11/1994 | Lubbers et al. |
| 5,372,133 | A | 12/1994 | Hogen Esch |
| 5,373,840 | A | 12/1994 | Knighton |
| 5,375,596 | A | 12/1994 | Twiss et al. |
| 5,415,181 | A | 5/1995 | Hogrefe et al. |
| 5,422,636 | A | 6/1995 | Urbas et al. |
| 5,429,132 | A | 7/1995 | Guy et al. |
| 5,443,066 | A | 8/1995 | Dumoulin et al. |
| 5,448,990 | A | 9/1995 | De Faria-Correa |
| 5,495,114 | A | 2/1996 | Adair |
| 5,603,687 | A | 2/1997 | Hori et al. |
| 5,604,531 | A | 2/1997 | Iddan et al. |
| 5,662,587 | A | 9/1997 | Grundfest et al. |
| 5,674,265 | A | 10/1997 | Deschampse et al. |
| 5,681,020 | A | 10/1997 | Buck |
| 5,681,260 | A * | 10/1997 | Ueda et al. ............... 600/114 |
| 5,819,736 | A | 10/1998 | Avny et al. |
| 5,860,916 | A * | 1/1999 | Pylant ....................... 600/208 |
| 5,993,378 | A | 11/1999 | Lemelson |
| 6,632,171 | B1 * | 10/2003 | Iddan et al. ............... 600/106 |
| 6,632,216 | B1 | 10/2003 | Houzego et al. |

FOREIGN PATENT DOCUMENTS

| | | |
|---|---|---|
| DE | 2629429 | 2/1980 |
| DE | 2929429 | 2/1980 |
| DE | 3440177 | 11/1984 |
| DE | 4037586 | 5/1992 |
| EP | 0248867 | 2/1991 |
| JP | 57-45833 | 3/1982 |
| JP | 61-122845 | 6/1986 |
| JP | 62-240038 | 10/1987 |
| JP | 2-36849 | 2/1990 |
| JP | 2-159254 | 2/1990 |
| JP | 3-136636 | 11/1991 |
| JP | 3-289779 | 12/1991 |
| JP | 4-109927 | 4/1992 |
| JP | 4-144533 | 5/1992 |
| JP | 4-180736 | 6/1992 |
| JP | 5-015515 | 1/1993 |
| JP | 5007573 | 1/1993 |
| JP | 6-114037 | 4/1994 |
| JP | 6-142081 | 5/1994 |
| JP | 6-285044 | 10/1994 |
| JP | 7-111985 | 5/1995 |
| JP | 11-341338 | 12/1999 |
| JP | 2001245844 | 9/2001 |
| RU | 1827167 | 7/1993 |
| WO | 87/03465 | 6/1987 |
| WO | 89/01722 | 2/1989 |
| WO | 92/19148 | 11/1992 |
| WO | 92/21307 | 12/1992 |
| WO | 94/05200 | 3/1994 |

OTHER PUBLICATIONS

"The Heidelburg pH Capsule System Telemetric Fasting Gastric Analysis," date unknown.

Fritscher-Ravens et al., "The Wireless Capsule: New Light in the Darkness," Digestive Diseases, vol. 20, No. 2, 2002.

Bio-Medical Telemetry: Sensing and transmitting Biological Information from Animals and Man, R. Stuart Mackay, John Wiley and Sons, New York, 1970, pp. 244-245.

Evan et al., "Studies of the Human Gastro-Intestinal Tract in the Ambulatory Subject using the pressure sensitive radiotelemetry capsule."

Lange et al. "Heidelberger Kapsel—ein Kleinstesender fur die pH-Messung im Magen," Telefunk-Zaitung, vol. 36, No. 5, 1963, pp. 265-270.

Manual of Photogrammetry, vol. 1, Third Edition, American Society of Photogrammetry, 1966, pp. 812-813.

P. Swain, "Wireless Capsule Endoscopy," Gut, vol. 52, (Suppl. IV), 2003, iv48-iv50.

Rowlands et al., "The Radio Pill: Telemetering from the Digestive Tract," British Communications and Electronics, Aug. 1960, pp. 598-601.

Leung et al., "Wireless Capsule Endoscopy in Chinese Patients with Suspected Small Bowel Diseases," Hong Kong Med J. vol. 10, 2004, pp. 179-183.

Yarbrough III et al., "Evaluation of the Heidelberg pH Capsule: Method of Tubeless Gastric Analysis," The American Journal of Surgery, vol. 117, Feb. 1969, pp. 185-192.

English language Abstract of JP 2-159254.
English language Abstract of JP 2-36849.
English language Abstract of JP 3-136636.
English language Abstract of JP 5-15515.
English language Abstract of JP 5-7573.
English language Abstract of JP 11-341338.
English language Abstract of JP 57-45833.
English language Abstract of JP 61-122845.
English language Abstract of JP 62-240038.

* cited by examiner

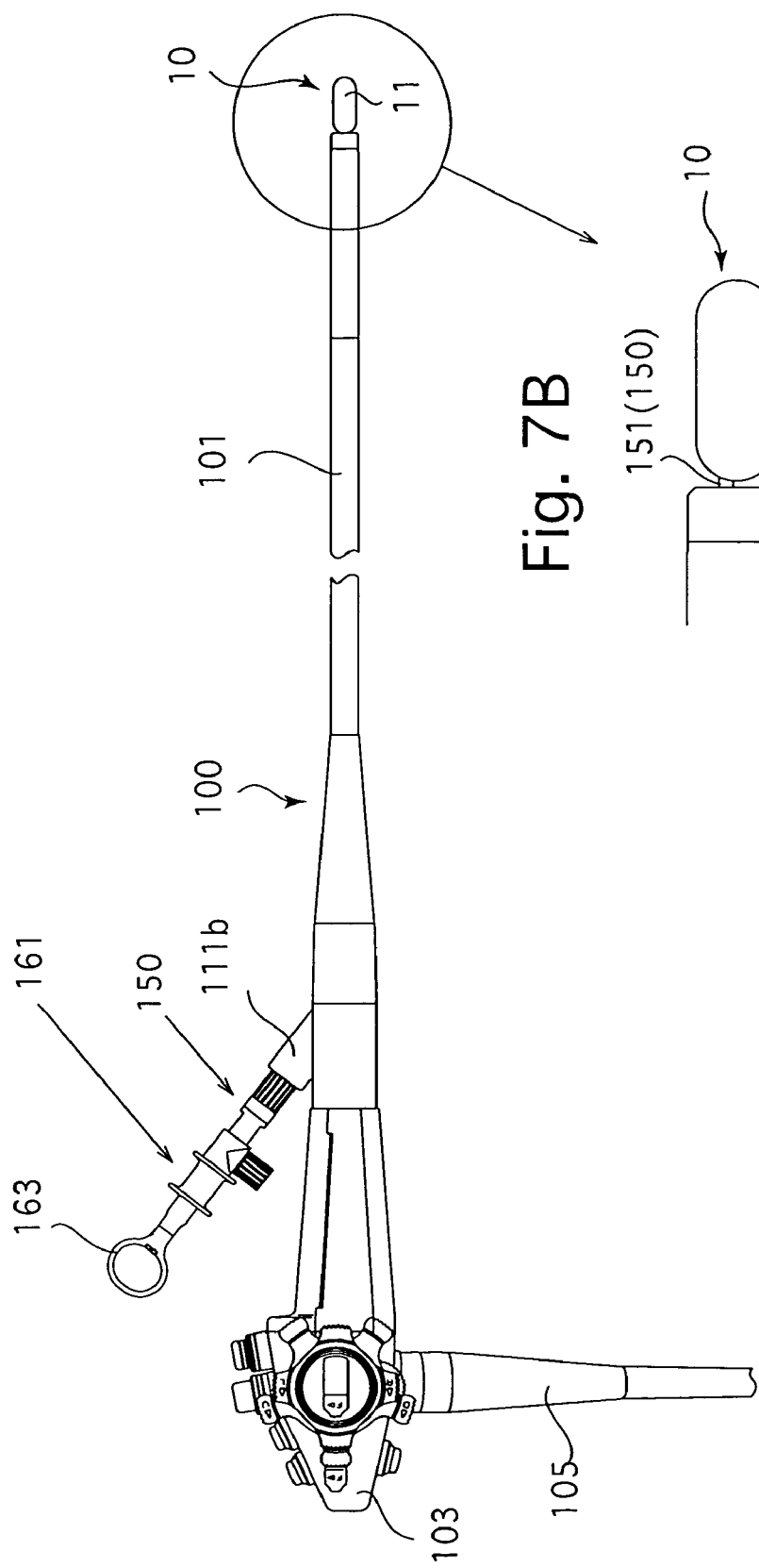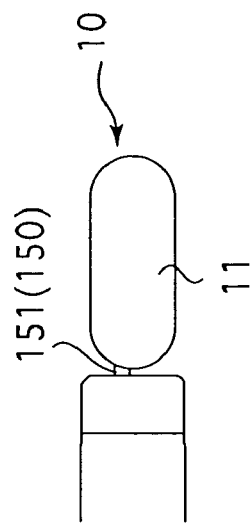

CAPSULE ENDOSCOPE GUIDANCE SYSTEM, CAPSULE ENDOSCOPE HOLDER, AND CAPSULE ENDOSCOPE

BACKGROUND OF THE INVENTION

1. Field of the Invention

The present invention relates to a capsule endoscope having external terminals, and a capsule endoscope guidance system and a capsule endoscope holder which are capable of holding such a capsule endoscope at a distal end of an endoscope, and the like, for guidance thereof.

2. Description of the Related Art

A capsule endoscope, which has been recently developed, captures images of the inside of a lumen (inside a patient's body) with an electronic camera equipped with a built-in image pickup device such as a CMOS image sensor while illuminating the inside of the lumen with a light source housed within a sealed capsule container. Thereafter, the capsule endoscope wirelessly transmits the captured image signals outside the patient's body. A processor for capsule observation, which is provided externally, receives the transmitted image signals so as to display the images on a screen of a monitor television or the like (JP 2001-245844 and the like). A user views this monitor television screen so as to observe and examine the state of a body cavity of the patient. Electronic parts in the capsule endoscope, such as the light source and the image pickup device, are powered by a battery included within the capsule container as a power source.

Such a capsule endoscope is orally inserted into the patient by swallowing the capsule endoscope so as to move from the esophagus through to the stomach, the duodenum and subsequently the small intestine. In the body cavity, the capsule endoscope is propelled by peristalsis of the intestines and the like. The capsule endoscope produces images with the electronic camera under the illumination of the light source as the capsule moves so as to wirelessly transmit the captured image signals.

For such a capsule endoscope without any self-advancing function and position control function, however, the user can not control how, and in which direction, the capsule endoscope advances after the capsule endoscope enters the body cavity of a patient. For example, as shown in FIG. 22 illustrating a human body, in the case where the first target application-position which is desired to be imaged, observed, examined, and the like, with the capsule endoscope, is distant from the mouth, it is impossible to know in which way and in which direction the capsule endoscope would reach the target application-position. Therefore, it cannot be ensured that the capsule endoscope reaches the target application-position with a sate desired by the user. Moreover, in the case where the first target application-position is distant from the mouth, a lot of time is wasted waiting for the capsule endoscope to reach the target application-position, thereby wasting the power of an internal battery for imaging, transmission and the like. Thus, the capacity of the internal battery needs be increased as much as possible.

SUMMARY OF THE INVENTION

The present invention is devised in view of the above-described problems of conventional capsule endoscopes, and provides a capsule endoscope guidance system and a capsule endoscope holder, which allow a user to place a capsule endoscope at the first target application-position desired by the user with a state desired by the user.

The present invention also provides, in the capsule endoscope guidance system, a capsule endoscope having external terminals that allow power to be supplied to the capsule endoscope from outside the patient's body until the capsule endoscope is positioned at a desired position in the body, and a capsule endoscope holder for such a capsule endoscope.

According to an aspect of the present invention, a capsule endoscope guidance system is provided, including a member having an elongated flexible portion which can be guided to a desired position in a body cavity of a patient's body by manipulating a distal end portion of the member wherein the elongated flexible portion bends in accordance with an operation at a proximal end portion of the member, including a capsule endoscope holding device, provided at a distal end of the elongated flexible portion, for removably holding a capsule endoscope; and a removal/attachment manipulation device provided on the proximal end portion, for manipulating removal and attachment of the capsule endoscope holding device.

It is desirable for the capsule endoscope holding device to include forceps inserted from the proximal end of the elongated flexible portion so as to project from the distal end thereof in order to hold a capsule endoscope.

The member having the elongated flexible portion can be an endoscope.

The capsule endoscope can include, in a water-proof sealed capsule container, an image pickup device; a driving signal output device for outputting a driving signal for driving the image pickup device; an illumination device for illuminating an object image is to be captured by the image pickup device; a transmission device for wirelessly transmitting a video signal, captured and output by the image pickup device, outside the water-proof sealed capsule container; and a power source for supplying electric power to the image pickup device, the driving signal output device, the illumination device, and the transmission device.

The capsule endoscope guidance system can further include a receiving device for receiving a video signal, the video signal being transmitted from the capsule endoscope by the transmission device; and a monitor apparatus for visualizing the video signal received by the receiving device. The receiving device and the monitor apparatus are provided externally, outside the patient's body.

It is desirable for the capsule endoscope holding device to be equipped with a power source supply device for supplying electric power to the capsule endoscope while holding the capsule endoscope.

It is desirable for the capsule endoscope holding device to be equipped with image pickup device driving signal output device for supplying an image pickup device driving signal to the capsule endoscope while holding the capsule endoscope.

It is desirable for the capsule endoscope holding device to be equipped with a video signal transmission device for receiving transmission of a video signal output from the capsule endoscope while holding the capsule endoscope.

It is desirable for the capsule endoscope to include a switching device for switching to an operation powered by an external power source supplied from the power source supply device while the capsule endoscope is held by the capsule endoscope holding device.

It is desirable for the capsule endoscope to include a switching device for switching a driving mode of the included image pickup device driven by an image pickup device driving signal, input from the capsule endoscope holding device, while the capsule endoscope is held by the capsule endoscope holding device.

It is desirable for the capsule endoscope to further include a detection device for detecting that the capsule endoscope is held by the capsule endoscope holding device; and a switching device for switching to an operation powered by an external power source supplied from the power source supply device when the detection device detects that the capsule endoscope is held by the capsule endoscope holding device.

It is desirable for the capsule endoscope to include a detection device for detecting that the capsule endoscope is held by the capsule endoscope holding device; and a switching device for switching an image pickup device driving signal for driving the included image pickup device driven by an image pickup device driving signal input from the capsule endoscope holding device when the detection device detects that the capsule endoscope is held by the capsule endoscope holding device.

In another embodiment, a capsule endoscope holder for removably engaging with an engaging portion formed in a capsule container of a capsule endoscope is provided, including a member having an elongated flexible portion which can bend in accordance with an operation at a proximal end of the member, the distal end of the flexible portion being inserted into the proximal end of the capsule endoscope, which is insertable into a patient's body, so that the capsule endoscope extends from the distal end of the flexible portion; and an engagement member provided at the distal end of the elongated flexible portion, for removably engaging with the engaging portion of the capsule endoscope.

In another embodiment, a capsule endoscope holder for holding a capsule endoscope including an engagement hole having a narrow opening formed in a sealed capsule container is provided, including a member having an elongated flexible portion which can bend in accordance with an operation at a proximal end of the member, the distal end of the flexible portion being inserted into the sealed capsule container, which is insertable into a patient's body, so that the sealed capsule container extends from the distal end of the flexible portion; and an openable/closeable engagement member provided at the distal end of the elongated flexible portion. The openable/closeable engagement member is inserted into the engagement hole in a closed state, is opened outwards inside the engagement hole to be engaged in the engagement hole so as not to be pulled out of the engagement hole. The openable/closeable engagement member is closed in order to be pulled out of the engagement hole.

It is desirable for the member of the capsule endoscope holder to be provided with a flexible pipe. The openable/closeable engagement member includes a movement manipulation member provided at the proximal end of the flexible pipe and a cable driven by the movement manipulation member, the movement manipulation member and the cable being slidably inserted into the flexible pipe.

The openable/closeable engagement member is attached to the distal end of the flexible pipe, the openable/closable engagement member being closed and opened by relative movement between the cable and the flexible pipe.

It is desirable for the sealed capsule container, which is insertable into the patient's body, to include an endoscope.

It is desirable for the openable/closable engagement member to include four connecting members; and a plate-like member driven by a cable so as to project from and be drawn back into the flexible pipe. The four connecting members constitute a quadric crank chain by a fixed shaft attached to the distal end of the flexible pipe and a driving shaft attached to the plate-like member, the fixed shaft and the driving shaft being relatively moveable to be away from each other and to approach each other. The fixed shaft and the driving shaft move away from each other and approach each other in a direction orthogonal to a moving direction of the plate-like member via movement of the plate-like member in projecting and drawing directions with respect to the flexible pipe.

When the openable/closable engaging member is inserted into the engagement hole, the plate-like member can project forwards from the distal end of the flexible pipe, and thereafter the plate-like member is relatively moved in a drawing direction with respect to the flexible pipe. Two connecting members, of the four connecting members, which are supported by the fixed shaft abut against a circumferential edge of an opening of the engagement hole while being opened in a direction wherein the fixed shaft and the driving shaft approach each other to draw the flexible pipe into the engagement hole to thereby close the opening with the flexible pipe to obtain a connected state.

When the plate-like member relatively moves with respect to the flexible pipe in a projecting direction in the connected state, the two connecting members supported by the fixed shaft can be closed in a direction wherein the fixed shaft and the driving shaft move away from each other while the distal end of the plate-like member presses a base of the engagement hole to, thereby disconnect the flexible pipe from the engagement hole.

The cable or the plate-like member can be biased by a spring member in a direction wherein the openable/closeable engagement member is opened.

In another embodiment, a capsule endoscope is provided, including an engagement hole having closed end, formed in a sealed capsule container of the capsule endoscope; and external terminals provided in the engagement hole, the external terminals being electrically conductive with an electrical wiring in the sealed capsule container, and the external terminals being electrically conductive with terminals of an engagement member inserted into the engagement hole.

It is desirable for the engagement hole to include a narrowed opening, and for the engagement hole to be enlarged toward the base.

The engagement member can include an elongated flexible portion which can bend in accordance with an operation at a proximal end thereof, wherein the distal end of the elongated flexible portion is inserted into the proximal end of a member which is insertable into a patient's body so that the distal end of the elongated flexible portion inserted into a patient's body is held by engagement between the engagement member and the engagement hole.

It is desirable for a switching device for starting and stopping electrical conduction between the external terminals and the electric wiring in the capsule container to be provided in the engagement hole. An operational portion of the switching device is provided at the base of the engagement hole. The switching device allows electrical conduction between the external terminals and the electric wiring in the capsule container while the engagement member is inserted into the engagement hole so as to active the operational portion.

In another embodiment, a capsule endoscope holder for holding a capsule endoscope is provided, including an engagement hole with a narrow opening, formed on an end of a capsule; and external terminals provided in the engagement hole, being electrically conductive with an electrical wiring in the capsule container, the capsule endoscope holder including an engagement member provided at a distal end of a flexible long member, the engagement member being inserted into the engagement hole in a closed state, the engagement member engaging with the engagement hole when the engagement member is opened within the engagement hole, whereas the engagement member is disengaged with the engagement hole when the engagement member is closed. The engagement member further includes terminals being electrically conductive with the corresponding external terminals in the engagement hole while the engagement member is inserted in the engagement hole.

The capsule endoscope holder can include the flexible long member having an elongated flexible portion which can bend in accordance with an operation at a proximal end thereof, wherein the distal end of the elongated flexible portion of the flexible long member is inserted into the proximal end of a member which is insertable into a patient's body; wherein the engagement member being provided at the distal end of the elongated flexible portion of the flexible long member. The engagement member is inserted into the engagement hole in a closed state to be opened within the engagement hole so as to engage with the engagement hole, and in order to disengage the engagement member, the engagement is closed to order to be drawn out of the engagement hole.

It is desirable for the flexible long member to include a flexible pipe. The engagement member can include a movement manipulation member provided at the proximal end of the flexible pipe and a cable driven by the movement manipulation member, the movement manipulation member and the cable being slidably inserted into the flexible pipe. The engagement member is attached to the distal end of the flexible pipe, wherein the engagement member is closed and opened via relative movement between the cable and the flexible pipe.

The openable/closable engagement member can include four connecting members; and a plate-like member driven by a cable so as to project from and be drawn back into the flexible pipe;

wherein the four connecting members constitute a quadric crank chain by a fixed shaft attached to the distal end of the flexible pipe and a driving shaft attached to the plate-like member, the fixed shaft and the driving shaft being relatively moveable in to be away from each other and to approach each other; and wherein the fixed shaft and the driving shaft move away from each other and approach each other in a direction orthogonal to a moving direction of the plate-like member via movement of the plate-like member in projecting and drawing directions with respect to the flexible pipe.

The terminals of the engagement member can be provided at predetermined intervals on a face of the plate-like member, opposite to a face where the fixed shaft is attached and the connecting members are positioned in a direction approximately orthogonal to a direction in which the plate-like member is inserted into and drawn out of the engagement hole. The external terminals of the capsule endoscope are provided on a surface of the engagement hole so as to correspond to the terminals of the plate-like member.

When the openable/closable engaging member is inserted into the engagement hole, the plate-like member can project forwards from the distal end of the flexible pipe, and thereafter the plate-like member is relatively moved in a drawing direction with respect to the flexible pipe. Two connecting members, of the four connecting members, which are supported by the fixed shaft abut against a circumferential edge of an opening of the engagement hole while being opened in a direction wherein the fixed shaft and the driving shaft approach each other to draw the flexible pipe into the engagement hole to thereby close the opening with the flexible pipe to obtain a connected state, whereby each of the terminals attached to the plate-like member is brought into an electrically conductive state with each of the external terminals provided in the engagement hole.

When the plate-like member relatively moves with respect to the flexible pipe in a projecting direction in the connected state, the two connecting members supported by the fixed shaft can be closed in a direction wherein the fixed shaft and the driving shaft move away from each other while the distal end of the plate-like member presses the base of the engagement hole, so that the terminals attached to the plate-like member are not electrically connected with the respective external terminals provided in the engagement hole, thereby separating the flexible pipe from the engagement hole.

It is desirable for an operational portion of a normally open switch device for starting and stopping electrical conduction between each of the external terminals provided in the engagement hole and an electronic member included in the capsule be provided at the base of the engagement hole, wherein the operational portion is pressed by the plate-like member in the connected state to be closed when the plate-like member is inserted into the engagement hole.

It is desirable for the external terminals to be connected to a driving signal switching circuit for driving a power source provided within the capsule container so that electric power is supplied from the terminals.

The external terminals can be connected to an image pickup device provided within the capsule container so that an image pickup device driving signal is supplied from the terminals.

The present disclosure relates to subject matter contained in Japanese Patent Application Nos. 2002-214494, 2002-214495, and 2002-214514 (all filed on Jul. 23, 2002) which is expressly incorporated herein by reference in its entirety.

BRIEF DESCRIPTION OF THE DRAWINGS

FIGS. 7A and 7B show a principal portion of a third embodiment of the capsule endoscope guidance system where an capsule endoscope holder according to the present invention is applied to an electronic endoscope;

DETAILED DESCRIPTION OF THE PREFERRED EMBODIMENTS

Figure 1:
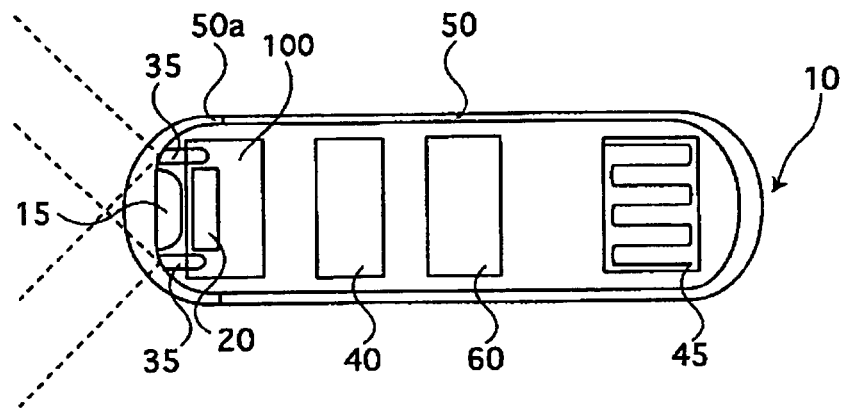
FIG. 1 is a schematic diagram showing a basic system configuration of a capsule endoscope to which the present invention is applied.

Hereinafter, the present invention will be described with reference to the illustrated embodiments. FIG. 1 shows a basic system configuration of a capsule endoscope to which the present invention is applied. A capsule endoscope guidance system includes a capsule endoscope 10 to be swallowed by a patient, and a capsule-observation processor 50 and a monitor television TV1 for observation which are provided outside the patient.

The capsule endoscope 10 includes, in an oval sealed (water tight/water proof) capsule container 11, an image sensor (e.g., a CMOS or a CCD) 13 acting as image pickup device; an image pickup device driving circuit 15 for driving the CMOS image sensor 13 to perform an image pickup operation; a signal transmission section (transmission device) 17 for wirelessly transmitting an image signal captured by the CMOS image sensor 13; light sources (illumination device) 19 such as LEDs, for illuminating an object to be imaged; and an internal power source 21 for supplying electric power to the above-mentioned electronic members. The CMOS image sensor 13 and the light sources 19 are placed on the shorter edge side of the sealed capsule container 11. Two, three or more light sources 19 are provided around the CMOS image sensor 13. Light-emitting diodes (LEDs) are normally used as the light sources 19. A cell, a rechargeable battery, or the like, is used as the internal power source 21.

The capsule endoscope 10 is inserted into a body cavity while the end thereof, where the CMOS image sensor 13 and the light sources 19 are provided, is oriented forward.

The capsule-observation processor 50 includes, in a processor cabinet 51, a signal receiving section (receiving device) 53 for receiving an image signal transmitted from the signal transmission section 17; and a capsule observation image processing circuit 55. A video signal which is processed by the capsule observation image processing circuit 55 is displayed on the monitor television TV1.

(0011)

Figure 2:
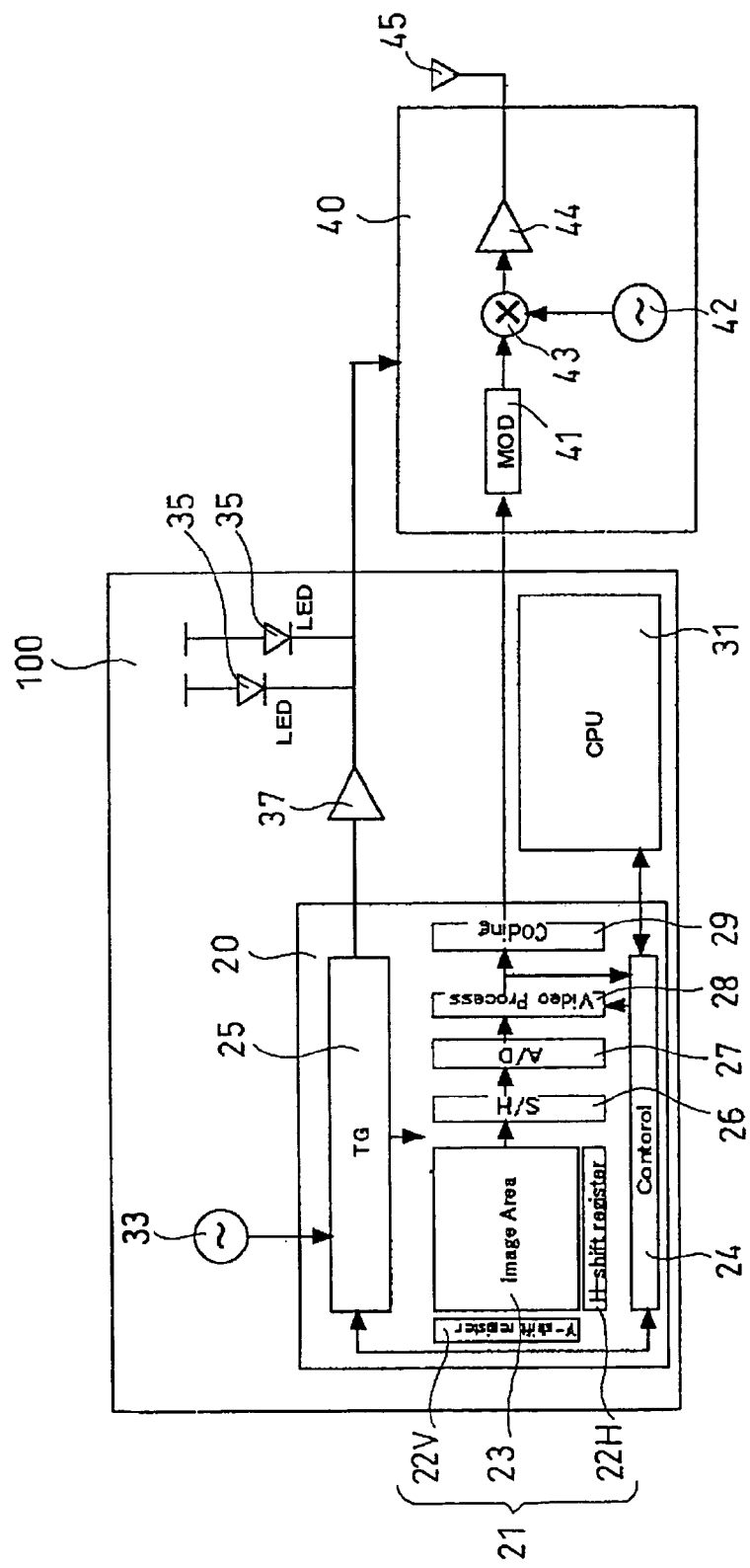
FIG. 2 is a schematic diagram showing a structure of a first embodiment of a capsule endoscope guidance system to which the present invention is applied.

A first embodiment of a capsule endoscope guidance system will be described with reference to a capsule endoscope guidance system shown in FIG. 2. The first embodiment of the capsule endoscope guidance system is characterized by the following structure. An electronic endoscope is used for the capsule endoscope 10 as a member having an elongated flexible portion that can be guided to a desired position in a body cavity by manipulating the distal end of the electronic endoscope so that the elongated flexible portion bends in accordance with an operation at the proximal end. The distal end of a scope of the electronic endoscope, which is inserted into the patient's body, is gripped with forceps provided within the endoscope. In such a gripped state, the electronic endoscope can be manipulated so as to be guided to a target application-position while images produced by the capsule endoscope or the electronic endoscope are observed on the monitor. The components having the same functions as those of the capsule endoscope and the processor for capsule observation shown in FIG. 1 are denoted by the same reference numerals in FIG. 2, and the details thereof are herein omitted.

In addition to the capsule endoscope 10 and the capsule-observation processor 50, the capsule endoscope guidance system includes a scope section (member) 100 and an endoscope processor section 200. The scope section 100 includes a flexible scope (elongated flexible portion) 101, a manipulation section 103, and a connection cable section 105 connected to the endoscope processor section 200. At a distal end of the scope 101, which is inserted into the patient's body, an electronic camera 107 functioning as image pickup device, an end face of a light guide 109 for illumination, and a forceps port 111 are provided.

Although not illustrated in detail, the electronic camera 107 includes, as conventionally known, an image pickup lens serving as an imaging optical system, and for example, a CCD image sensor serving as an image pickup device. The electronic camera 107 is operated by a driving signal transmitted from the endoscope processor section 200 via an image pickup device driving signal line 113. A captured video signal is output via a video signal line 115 to the endoscope processor section 200. The light guide 109 guides illumination light, which is emitted from a light source 209 included in the endoscope processor section 200, to a portion inserted into the patient's body. Thereafter, the illumination light is emitted from a distal end face of the light guide 109, which is inserted into the patient's body.

The forceps port 111a is communicatively connected with a forceps insertion port 111b provided for a portion of the scope 101 outside the patient's body. The capsule endoscope 10 is gripped with forceps 121, of capsule gripping forceps 120 which are inserted from the forceps insertion port 111b, and the distal end of the forceps 121 projects from the forceps port 111a.

As a gripping structure of the forceps 121 for the capsule endoscope 10, for example, the following a mechanical engagement structure or a magnetically attracting structure can be used. In a mechanical engagement structure, the forceps 121 are provided with claws, and the sealed capsule container 11 is provided with concave portions so as to allow the engagement of the claws with the concave portions. In a magnetically attracting structure, electromagnets are provided at the distal end of the forceps 121, and a magnetic member attracted to the electromagnets is provided on a rear end face of the sealed capsule container 11 so as to allow the magnetic member to be attracted to the electromagnets by magnetic force.

The gripping and releasing operations of the forceps 121 for the capsule endoscope 10 are effected by manipulating a handle 123 provided outside the patient's body.

The scope section 100 is connected to the endoscope processor section 200 via the connection cable section 105. The endoscope processor section 200 includes, inside the processor cabinet 201, a system controller 203 for controlling the entire endoscope system; a timing controller 205 for generating a timing signal; a video signal processing circuit 207; the light source 209; and a power source section 211 for supplying electric power to these members and the electronic components of the entire system. The video signal processing circuit 207 performs color adjustment and contour emphasis processing on a video signal, which is input through a video signal line 115, so as to convert the video signal into a video signal that can be displayed on a monitor television TV2 or a video signal that can be processed in a data system or the like.

The system controller 203 controls the operations of the electronic camera 107, the video signal processing circuit 207 or the like, based on a timing signal (a clock or a pulse) generated by the timing controller 205. For instance, the system controller 203 generates an image pickup device driving signal based on the timing signal so as to control an imaging operation of the electronic camera 107 in accordance with the image pickup device driving signal.

Light emitted from the light source 209 is incident on the end face of the light guide 109 to exit from the tip end face of the light guide 109 which is situated at the distal end of the scope 101, thereby illuminating the inside of a body cavity. The electronic camera 107 is driven under this illumination. A video signal captured by the electronic camera 107 is input to the endoscope processor section 200 via the video signal line 115. The light source 209 of the endoscope processor section 200 is equipped with a shutter 209S for switching the ON/OFF control of the illumination without directly switching the ON/OFF control of the light source.

The video signal output from the video signal processing circuit 207 is input to a video input terminal of the monitor television TV2 so as to be displayed on the monitor television TV2.

The capsule endoscope guidance system of the first embodiment is used in the following manner. The scope section 100 is connected to the endoscope processor section 200, and the forceps 121 are inserted through the forceps insertion port 111b to project beyond the forceps port 111a, thereby gripping the capsule endoscope 10. In a state where the forceps 121 are gripping the capsule endoscope 10, the capsule-observation processor 50 and the monitor television TV1 are turned ON. As a result, after the CMOS image sensor 13 produces images, a video signal wirelessly transmitted from the signal transmission section 17 is received by the capsule-observation processor 50 so as to be viewed on the monitor television TV1.

The user (e.g., a physician) manipulates the scope section 100 to insert the capsule endoscope 10 through the patient's mouth. The user manipulates the scope section 100 while observing images displayed on the monitor television TV1 so as to guide the capsule endoscope 10 to a target application-position.

When the user confirms that the capsule endoscope 10 reaches the target application-position, the user manipulates the handle 123 so as to release the capsule endoscope 10 from the forceps 121 to leave the capsule endoscope 10 at the target application-position. Thereafter, since the user can view the images produced by the electronic camera 107 of the scope section 100 on the monitor television TV2, the user can manipulate the scope section 100 while the user observes the images on the monitor television TV2, so as to safely pull out the scope 101 from the patient's body cavity.

Thereafter, the capsule endoscope 10 continues transmitting images of the inner face of a lumen, which are produced by the CMOS image sensor 13, via the signal transmission section 17, while being propelled by peristalsis of the small intestine and the like.

As described above, according to the first embodiment of the capsule endoscope guidance system, since it is ensured that the capsule endoscope 10 is guided to a target application-position by using the existing scope section 100, endoscope processor section 200, and capsule gripping forceps 120, a state of the target application-position can be reliably observed.

In the first embodiment of the capsule endoscope guidance system, it is ensured that the capsule endoscope 10 can be guided to a target application-position distant from the patient's mouth, such as inside the small intestine, while the user is observing images produced by the electronic camera 107 of the scope section 100 on the monitor television TV2 rather than images produced by the CMOS image sensor 103 of the capsule endoscope 10.

Although the electronic endoscope is used as an endoscope for guiding the capsule endoscope 10 in the first embodiment of the capsule endoscope guidance system, an optical endoscope can be used instead. In other words, any type of endoscope can be used as long as the endoscope is capable of gripping the capsule endoscope 10 to guide the capsule endoscope 10 to a target application-position inside a lumen.

The capsule endoscope 10 normally includes a cell or rechargeable battery as an internal power source. In addition, since the capsule endoscope 10 is extremely compact, the size of the battery or cell is correspondingly limited, which prevents the capacity from being sufficiently increased. Therefore, there is a possibility that the capacity of the battery/cell may run out from the capsule endoscope 10 being inserted to being excreted.

In view of this risk, a second embodiment of the capsule endoscope guidance system provides a capsule endoscope guidance system so that an internal power source of the capsule endoscope 10 is used as little as possible during the guidance of the capsule endoscope 10 to a target position. The second embodiment of the capsule endoscope guidance system will be described with reference to FIGS. 3 to 6B. The same components and the components having the same functions as those of the first embodiment of the capsule endoscope guidance system are denoted by the same reference numerals.

The capsule gripping forceps 120 include a driving power source line 125, an image pickup device driving signal line 127, and a video signal line 129. The driving power source line 125, the image pickup device driving signal line 127, and the video signal line 129 serve to connect the capsule-observation processor 50 to the capsule endoscope 10. When the capsule gripping forceps 120 are connected to the capsule-observation processor 50, each of the driving power source line 125, the image pickup device driving signal line 127, and the video signal line 129 is connected to each corresponding circuit included in the capsule-observation processor 50. When the forceps 121 grip the capsule endoscope 10, each of the driving power source line 125, the image pickup device driving signal line 127, and the video signal line 129 is connected to each of corresponding circuits included in the capsule endoscope 10. In other words, the respective corresponding circuits of the capsule-observation processor 50 and the capsule endoscope 10 are connected to each other through the respective driving power source line 125, the image pickup device driving signal line 127, and the video signal line 129.

In addition to the basic circuit shown in FIG. 1, the capsule-observation processor 50 includes a system controller 57 for controlling the capsule endoscope guidance system, a timing controller 59, and a capsule driving power source 61. The system controller 57 generates an image pickup device driving signal based on a timing signal generated by the timing controller 59 so as to drive the CMOS image sensor 13 of the capsule endoscope 10 via the image pickup device driving signal line 127. The capsule driving power source 61 transfers capsule driving electric power to the capsule endoscope 10 via the driving power source line 125 so as to operate each of the circuits in the capsule endoscope 10. A video signal of the image captured by the CMOS image sensor 13 of the capsule endoscope 10 is input to the capsule observation image processing circuit 55 via the video signal line 129. The capsule observation image processing circuit 55 performs predetermined correction on the input signal so as to convert the input signal to a video signal which is compatible for inputting to the monitor television TV2. The obtained video signal is then output to the image switching device 301. The image switching device 301 performs a switching operation based on an image switching signal output from the system controller 57 via the image switching signal line 305. The system controller 57 receives a system control signal from the system controller 203 of the endoscope processor section 200 via the system control signal line 303 so as to control a switching operation so as to either display a video signal output from the endoscope processor section 200 (a video signal from the electronic camera 107) or display a video signal from the CMOS image sensor 13.

Figure 4:
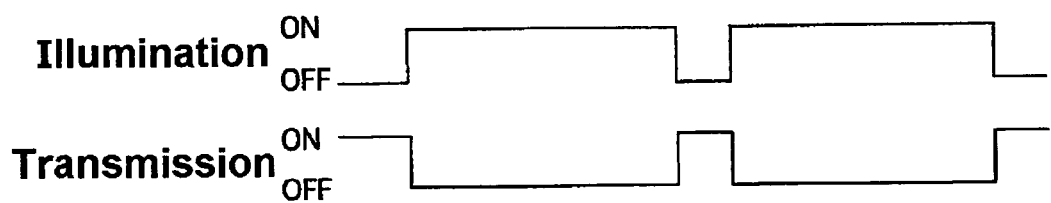
FIG. 4 is a block diagram showing an embodiment of a capsule endoscope applied to the second embodiment of the capsule endoscope guidance system to which the present invention is applied.

A more detailed structure of the capsule endoscope 10 used in the second embodiment is shown in FIG. 4. The same components and the components having the same functions as those of the capsule endoscope 10 shown in FIGS. 1 and 2 are denoted by the same reference numerals in FIG. 4.

The capsule endoscope 10 in this embodiment includes a power source switching circuit 23 and an operation switching circuit 25. The power source switching circuit 23 switches an operation power source of built-in circuits between the internal power source 21 and an external power source. The operation switching circuit 25 switches an operation mode of the built-in circuits between an internal power source mode and an external power source mode.

In the illustrated embodiment, the internal power source mode is a mode in which the built-in circuits are operated by electric power supplied from the internal power source 21. In the internal power source mode, the image pickup device driving circuit 15 is intermittently activated to intermittently operate the CMOS image sensor 13 via the image pickup device driving signal switching circuit (driving signal output device) 27 so as to transmit a video signal output from the CMOS image sensor 13 to the signal transmission section 17 via the video signal output switching circuit 29 where the video signal is modulated to a wireless signal so as to be output therefrom. In other words, the internal power source mode is a normal operation mode of the capsule endoscope 10.

The external power source mode is a mode in which the built-in circuits are operated in response to the supply of driving electric power (external power source) via the driving power source line 125. For example, when the supplied external power source is input to the power source switching circuit 23 and the operation switching circuit 25, the power source switching circuit 25 is switched from an internal power source operation to an external power source operation. As a result, the power source switching circuit 23 switches OFF the internal power source 21 so as to enter the external power source mode in which an external power source is supplied to each of the included components and circuits. Furthermore, the image pickup device driving signal switching circuit 27 is switched to perform an external image pickup device driving signal operation so that an image pickup device driving signal is input via the image pickup device driving signal line 127 to the CMOS image sensor 13. As a result, the CMOS image sensor 13 performs an image pickup operation. A video signal output from the CMOS image sensor 13 is output via the video signal output switching circuit 29 to the external video signal line 129 (capsule observation image processing circuit). In other words, the external power source mode is an operation mode in which the capsule endoscope 10 is being gripped by the forceps 121.

An operation for guiding the capsule endoscope 10 to a target application-position by using the capsule gripping forceps 120 will be described below.

When the capsule endoscope 10 is gripped with the forceps 121, the capsule endoscope 10 receives driving electric power (external power source) supplied via the driving power source line 125 as well as an image pickup device driving signal supplied via the image pickup device driving signal line 127 so as to start the operation in the external power source mode. Subsequently, a video signal of the image captured by the CMOS image sensor 13 is output via the video signal line 129 to the capsule-observation processor 50.

The capsule-observation processor 50 supplies driving electric power for the connected capsule gripping forceps 120 from the capsule driving power source 61 to the driving power source line 125, and the capsule-observation processor 50 supplies an image pickup device driving signal from the timing controller 59 to the image pickup device driving signal line 127. Thereafter, a video signal output from the video signal line 129 is input to the capsule observation image processing circuit 55 so as to be output to the image switching signal line 305 as a capsule observation video signal. Subsequently, the capsule observation video signal is input via the image switching device 301 to the monitor television TV2 where an image is viewed on the screen.

The user manipulates the scope section 100 with viewing an observation image displayed on the monitor television TV2 to guide the capsule endoscope 10 to a target application-position. After the capsule endoscope 10 is guided to the target application-position, the user manipulates the handle 123 to release the capsule endoscope 10 from the forceps 121 so as to leave the capsule endoscope 10 at the target application-position. When the capsule endoscope 10 has been released, the user operates the image switching device 301 so that the image produced by the electronic camera 107 can be displayed on the monitor television TV2. Accordingly, the user can safely pull out the scope 101 from the patient's body cavity while observing the images on the monitor television TV2.

Upon the user taking the scope 101 out of the patient, the user operates the image switching device 301 so that the images produced by the capsule endoscope 10 are displayed on the monitor television TV2.

Since the supply of external driving electric power is stopped for the capsule endoscope 10 which is released from the forceps 121, the power source is switched to the internal power source 21 so that the operation switching circuit 25 is switched to be operated in the internal power source operation mode, thereby starting its own capsule endoscope operation. Accordingly, since the capsule endoscope 10 can start its own capsule endoscope operation, a video signal produced by the CMOS image sensor 13 can be displayed on the monitor television TV2.

Figure 5:
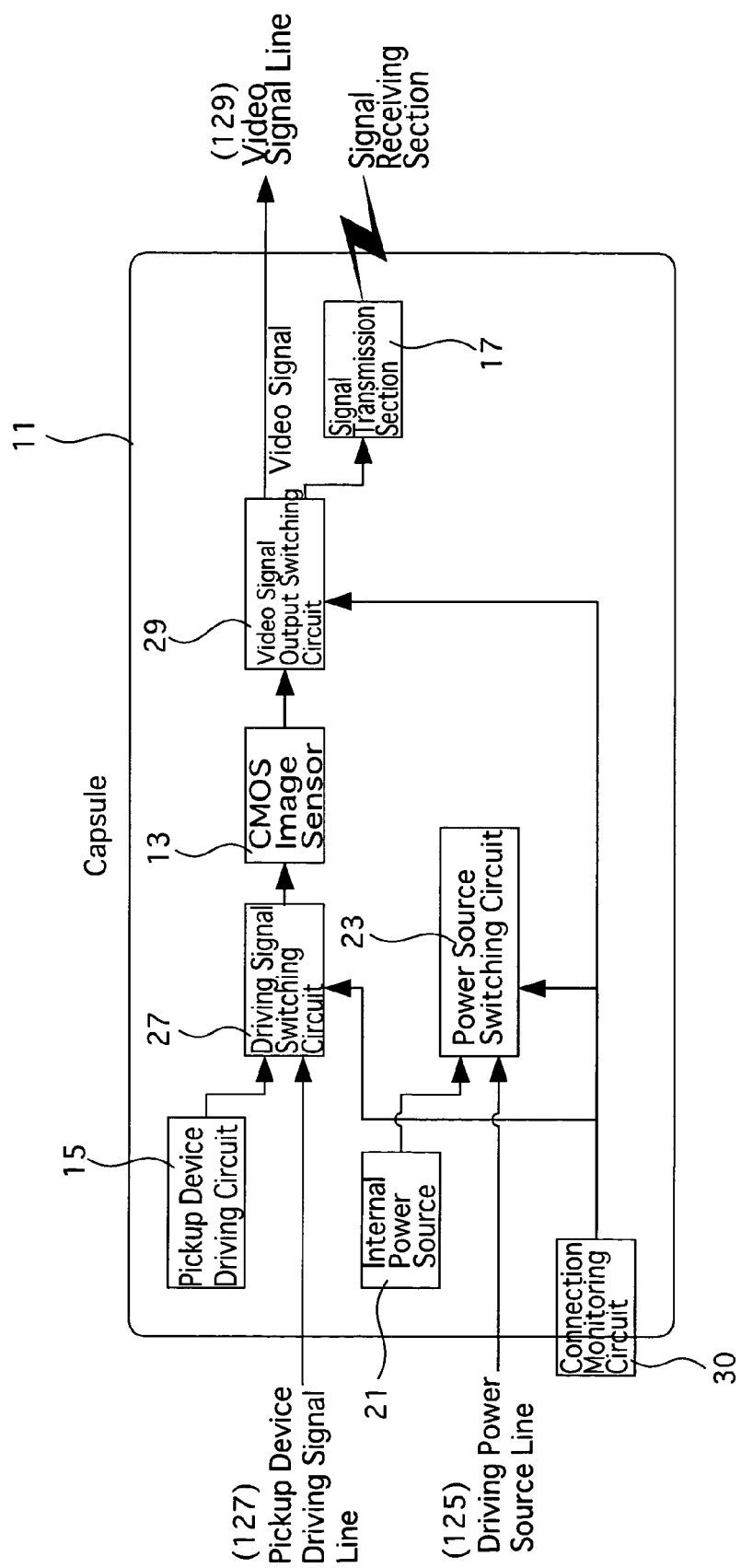
FIG. 5 is a block diagram showing another embodiment of a capsule endoscope applied to the second embodiment of the capsule endoscope guidance system to which the present invention is applied.

FIG. 5 is a block diagram showing principal circuits of another embodiment of the capsule endoscope 10. In the second embodiment of the capsule endoscope 10, the operation switching circuit 25 detects the supply of driving electric power so that the power source switching circuit 23 switches the operation mode from the internal power source operation mode to the external power source operation mode. In this embodiment of the capsule endoscope 10, the mode switching is detected by a forceps connection monitoring circuit (detection device) 30 so that the power source switching circuit 23 switches its power source.

Figure 6A:
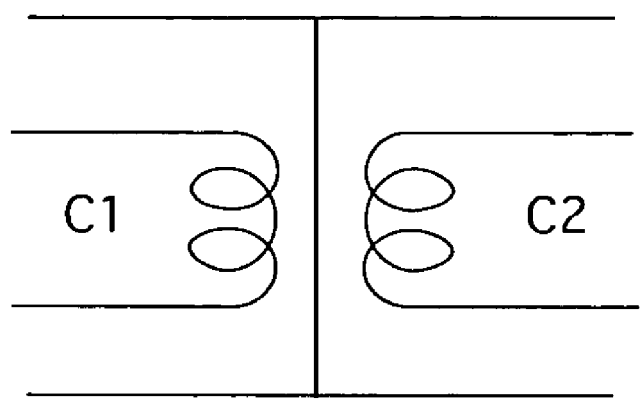
FIGS. 6A and 6B each shows an embodiment of a power source and signal transmission insulating structure between a capsule endoscope and capsule endoscope gripping forceps in a capsule endoscope guidance system to which the present invention is applied.
Figure 6B:
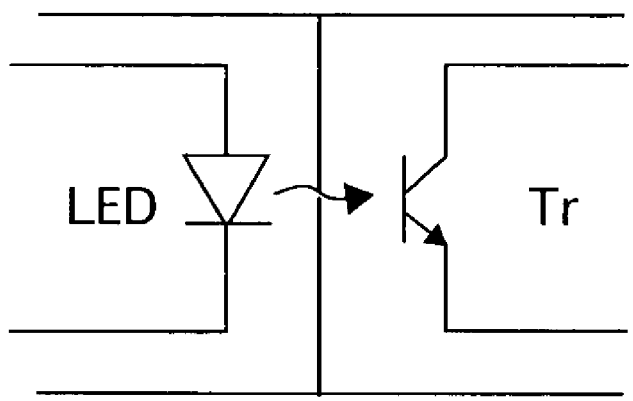

Examples of an insulating connection structure between the driving power source line 125, the image pickup device driving signal line 127 and the video signal line 129, and the capsule endoscope 10 are shown in FIGS. 6A and 6B.

A power source transfer system is a structure utilizing an electromagnetic induction effect of a coil. For example, as shown in FIG. 6A, a primary coil C1 included in a tip portion of the driving power source line 125 and a secondary coil C2 included in the capsule endoscope 10 are brought close to each other so that an alternating current flowing through the primary coil C1 generates an induced current in the secondary coil C2. In this embodiment, such a structure is utilized as an insulating structure for transferring driving electric power and an image pickup device driving signal.

A video signal transfer system is a structure utilizing optical communication using a light-emitting diode LED on the output side thereof and a photo-transistor Tr on the input side thereof, as shown in FIG. 6B. In this embodiment, this structure is used as an insulating structure including the light-emitting diode LED in the capsule endoscope 10 so as to transmit a video signal output from the video signal output switching circuit 29 to the video signal line 129.

Although the electronic endoscope (electronic scope) has been described as an endoscope in the above illustrated embodiments, the present invention is also applicable to an optical fiber constituted by an optical element. In the case where the present invention is applied to an optical fiber, such an optical fiber can be used as an electronic endoscope using the CMOS image sensor 13 of the capsule endoscope 10.

A capsule endoscope holder applicable to the above-described capsule endoscope guidance system will be described. Since the basic structures of a capsule endoscope, an electronic endoscope and a processor section for endoscope are the same as those of the capsule endoscope 10, the scope section 100 and the endoscope processor section 200 that have been already described based on FIGS. 1 to 6B, the description thereof is herein omitted. Furthermore, the same components and the components having the same functions as those described above are denoted by the same reference numerals, and the description thereof is herein omitted.

FIG. 7A is a front view showing a state where the capsule endoscope 10 is held at the distal end of the scope 101 via capsule connecting forceps 150. FIG. 7B is an enlarged view of a connected portion between the capsule endoscope 10 and the capsule connecting forceps 150. The forceps port 111a is in communication with the forceps insertion port 111b provided for a portion of the scope 101 outside the patient's body via a pipe (not shown). An engagement holder (openable/closeable engagement member) 151 for connecting and holding the capsule endoscope 10 is attached to the distal end of the capsule connecting forceps 150. The engagement holder 151 inserted from the forceps insertion port 111b projects beyond the forceps port 111a. The capsule endoscope 10 is connected to the thus projecting engagement holder 151. In other words, the capsule endoscope 10 is held at the distal end of the scope 101, which is inserted into the patient's body. The connecting and releasing operations of the capsule endoscope 10 via the engagement holder 151 are performed by manipulation of a manipulation section (removal/attachment manipulation device) 161 that is provided externally (i.e., outside the patient's body).

A connection structure between the capsule connecting forceps 150 and the capsule endoscope 10 will be described in further detail with reference to FIGS. 8A to 12.

An engagement hole 12 for connection (see FIG. 11) is formed in the center of a rear end face of the sealed capsule container 11 of the capsule endoscope 10, which is opposite to the end face provided with the CMOS image sensor 13 and the light source 19. The engagement hole 12 has a narrowed opening 12a and an enlarged hole 12b which enlarges from the opening 12a toward the base thereof. An inclined face 12c extending from the opening 12a toward the base thereof is formed between the opening 12a and the enlarged hole 12b. The engagement hole 12 in this embodiment is formed so that the opening 12a is sealed by an edge of the opening 12a and an outer circumferential face of a forceps pipe 153 in close contact with each other when the forceps pipe 153 is inserted into the opening 12a. In other words, the forceps pipe 153 is formed so as to serve as a sealing plug of the opening 12a.

The capsule connecting forceps 150 are provided with the engagement holder 151 to which a quadric crank chain mechanism is applied for connecting and holding the capsule endoscope 10. In the engagement holder 151, a cable 157 is slidably inserted through the forceps pipe 153, and the capsule endoscope 10 is connected and held at the distal end of the forceps pipe 153. The engagement holder 151 includes four connecting plates 158a, 158b, 158c and 158d having identical widths and lengths, as principal connecting members. The connecting plates 158a to 158d are connected to each other in a circular form so that adjacent two plates are connect with a pair by four shafts 159a, 159b, 159c, and 159d. The shaft 159a is a fixed shaft fixed to a projecting piece 154 provided on the distal end of the forceps pipe 153. The shaft 159c opposed to the fixed shaft 159a serves as a driving shaft fixed to the tip of a driving plate 155 (see FIG. 10) insertably housed within the forceps pipe 153. The driving plate 155 serves as a plate-like member that movably projects from the distal end of the forceps pipe 153 in projecting and retracting directions. The opposed shafts 159b and 159d between these shafts 159a and 159c serve as moving shafts. The distance between the moving shafts 159b and 159d varies in correspondence with a variation in distance between the shafts 159a and 159c. When the distance between the shafts 159a and 159c is increased, the distance between the shafts 159b and 159d decreases, and vice versa. The connecting plates 158a and 158d and the moving shafts 159b and 159d constitute an engaging portion.

An end of the driving plate 155, which is provided in the forceps pipe 153, is connected to one end (distal end) of the cable 157 which is slidably inserted into the forceps pipe 153. The other end (proximal end) of the cable 157 is connected to the handle 163 inserted from the end of the forceps pipe 153, which is provided outside the patient's body. The manipulation portion 161 is slidably attached to a portion of the forceps pipe 153 which is provided outside the patient's body. A tubular flange lever (movement manipulation member) 165 is connected to the end of the forceps pipe 153, which projects from the manipulation portion 161, outside the patient's body so as to be slidable with respect to the manipulation section 161. The manipulation portion 161 is fitted and held into the forceps insertion port 111b while the forceps pipe 153 is inserted through the forceps insertion port 111b with the engagement holder 151 projecting from the forceps port 111a. In other words, the length of the capsule connection forceps 150 is set so as to match a length from the forceps insertion port 111b to the forceps port 111a.

Figure 8A:
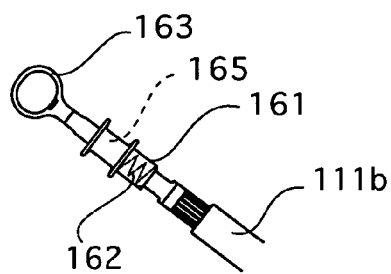
FIGS. 8A and 8B show principal portions of an embodiment of a capsule endoscope holder to which the present invention is applied, in a natural state.
Figure 8B:
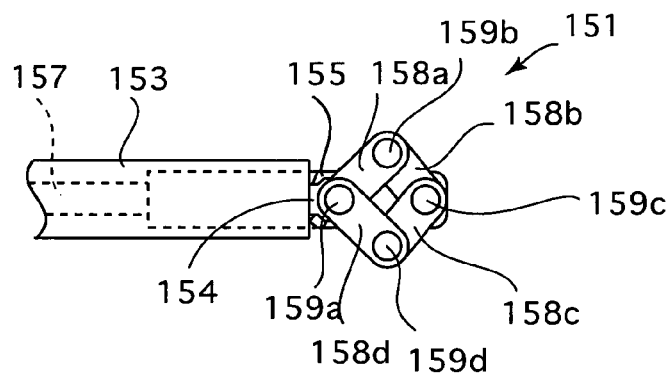
Figure 12:
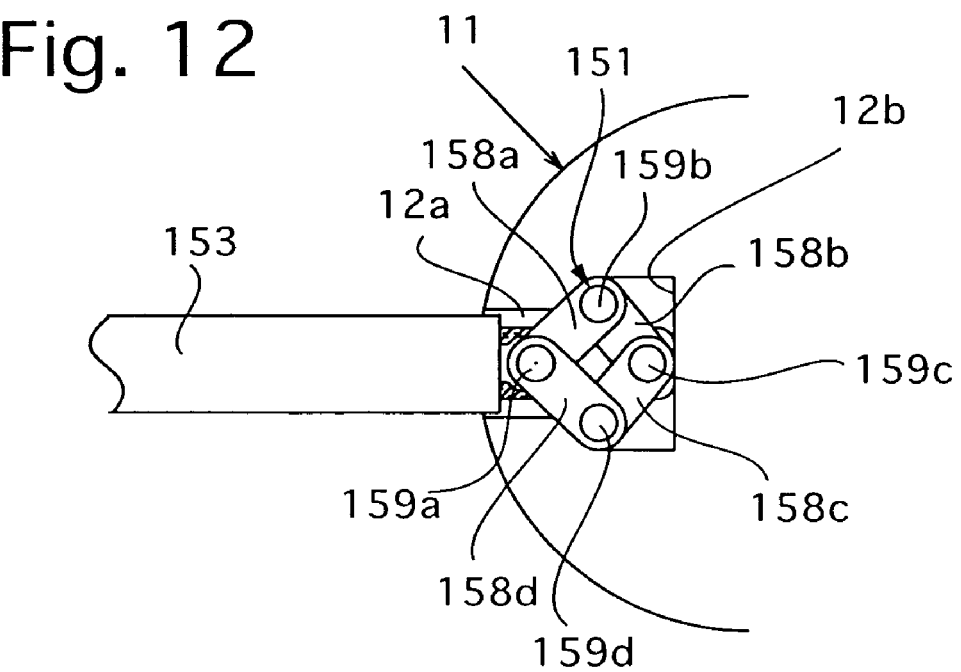
FIG. 12 is a view showing a state where the capsule endoscope is connected to the capsule endoscope holder.

Furthermore, the handle 163 and the manipulation portion 161 are connected to each other so as to prevent relative movement thereof, and as a result, the distance between the handle 163 and the flange lever 165 is increased between the manipulation portion 161 or the handle 163 and the flange lever 165 so as to bias the driving plate 155 into the forceps pipe 153. Therefore, the engagement holder 151 is held in a normally open state (FIGS. 8B and 12). When the flange lever 165 is pulled from/pushed to the manipulation portion 161 in this attached state, the forceps pipe 153 and the driving plate 155 relatively move, i.e., the driving plate 155 moves so as to project from/be drawn back into the forceps pipe 153 so that the connecting shaft 159c moves away from/approaches the connecting shaft 159a, respectively. As a result, the distance between the connecting shafts 159b and 159d is reduced or increased. For manipulation, the user puts his/her thumb into the handle 163, holds the flange lever 165 with an index finger and a middle finger, and then brings the thumb, the index finger, and the middle finger close to each other to pull the flange lever 165 toward the handle 163. Accordingly, the forceps pipe 153 is drawn back so that the driving plate 155 projects from the forceps pipe 153.

Figure 9A:
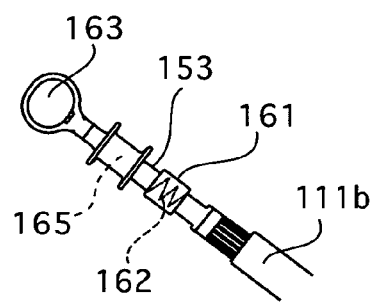
FIGS. 9A and 9B show principal portions of an embodiment of the capsule endoscope holder in its released state.
Figure 9B:
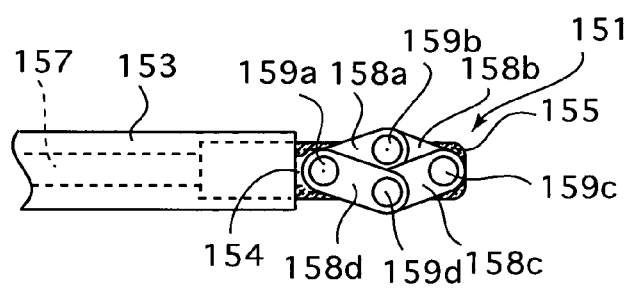
Figure 10:
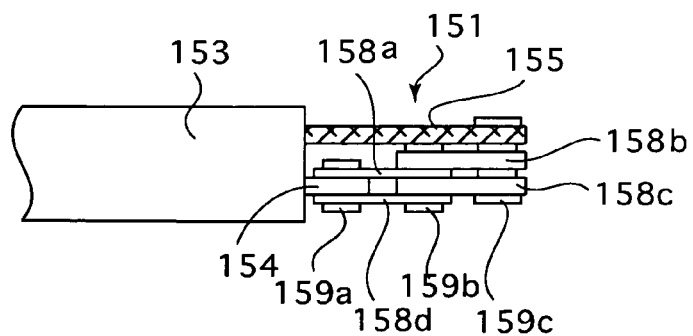
FIG. 10 is a view showing a top face of the capsule endoscope holder.
Figure 11:
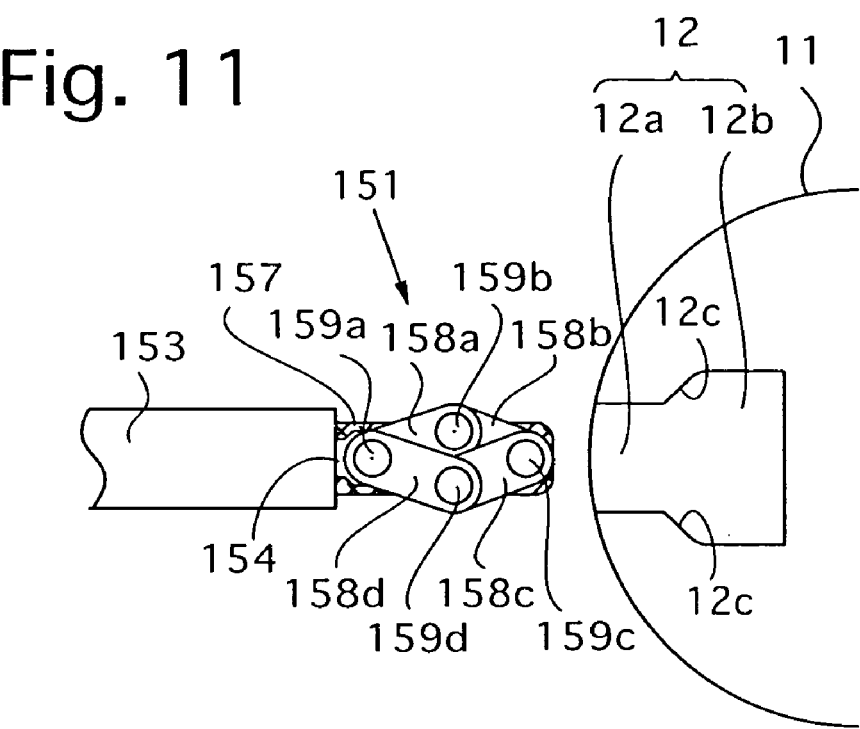
FIG. 11 is a view showing a state before a capsule endoscope is connected to the capsule endoscope holder.

When the driving plate 155 moves so as to project from an opening at the distal end of the forceps pipe 153, the distance between the shafts 159a and 159c is increased to narrow the distance between the shafts 159b and 159d (FIGS. 9B, 10 and 11). When the driving plate 155 moves so as to be drawn back into the forceps pipe 153, the distance between the shafts 159a and 159c is narrowed to increase the distance between the shafts 159b and 159d (FIGS. 8B and 12). In this embodiment, since the driving plate 155 is biased so as to be drawn back into the forceps pipe 153, the driving plate 155 is drawn back into the forceps pipe 153 due to biasing force of a spring 162 in a natural state, thereby opening out the engagement holder 151 in a direction perpendicular to the direction of movement of the driving plate 155 (FIGS. 8B and 12).

This capsule endoscope connection mechanism is used in the following manner. The engagement holder 151 is inserted through the forceps insertion port 111b into the scope section 100 connected to the endoscope processor section 200 so as to project from the forceps port 111a. At this time, the flange lever 165 is pulled so as to bring the engagement holder 151 into a closed (folded, or reduced in width) state (FIGS. 9A, 9B and 11). If the manipulation portion 161 is provided with a lock mechanism in such a manner that a pull of the flange lever 165 locks the flange lever 165 to prevent the flange lever 165 from projecting from the manipulation portion 161 by the biasing force of the spring 162, and unlocking allows the flange lever 165 to move so that the engagement holder 151 projects due to the biasing force of the spring 162, only one pull of the flange lever 165 allows the grasp to be released from the flange lever 165 when the capsule endoscope 10 is to be attached. Alternatively, the biasing direction of the spring 162 and the direction in which the lock mechanism acts can be opposite to each other. The engagement holder 151 can be always biased so as to project to be closed by the spring 162. In this case, when the flange lever 165 is pulled, the flange lever 165 is locked by the lock mechanism to maintain the engagement holder 151 in a opened state.

The engagement holder 151 in a closed state is inserted into the engagement hole 12 of the capsule endoscope 10, as shown in FIG. 11. Thereafter, the force for holding the handle 163 is released while the end of the engagement holder 151 is inserted to abut against the base of the engagement hole 12, thereby the engagement holder 151 is opened (increasing in width) via the biasing force of the spring 162 (FIG. 12). Namely, since the driving plate 155 moves so as to be drawn back into the forceps pipe 153, the distance between the moving shafts 159b and 159d is increased, thereby widely increasing an angle formed by the connecting plates 158a and 158d. In this manner, the driving plate 155 presses the inclined face 12c between the opening 12a and the enlarged hole 12b (so as to press the driving plate 155 against the base of the enlarged hole 12b) thereby preventing the engagement holder 151 from being pulled out of the opening 12a. Owing to this opening action of the engagement holder 151, the connecting plates 158a to 158d are opened out within the enlarged hole 12b to be larger than the diameter of the opening 12a. As a result, the engagement holder 151 is brought into a connected state so as not to be pulled out of the opening 12a. At the same time, the capsule endoscope 10 is connected and held at the tip of the scope 101 that is inserted into the patient's body while preventing the clattering movement by the force of the connecting plates 158a and 158d and the driving plate 155 for pressing the inner surface of the enlarged hole 12b. The engagement hole 12 is formed outside the sealed capsule container 11 so as to maintain a sealed state in the capsule.

In this connected state, the CMOS image sensor 13 performs an image pickup operation. A captured video signal is wirelessly transmitted by the signal transmission section 17 to be received by the signal receiving section 53 of the capsule-observation processor 50. Thereafter, the video signal is subjected to predetermined processing in the capsule observation image processing circuit 55 so as to be viewed on the monitor television TV1. The user inserts the capsule endoscope 10 through the patient's mouth. The user manipulates the scope 101 to guide the capsule endoscope 10 to a target position while viewing the images displayed on the screen of the monitor television TV1.

Figure 22:
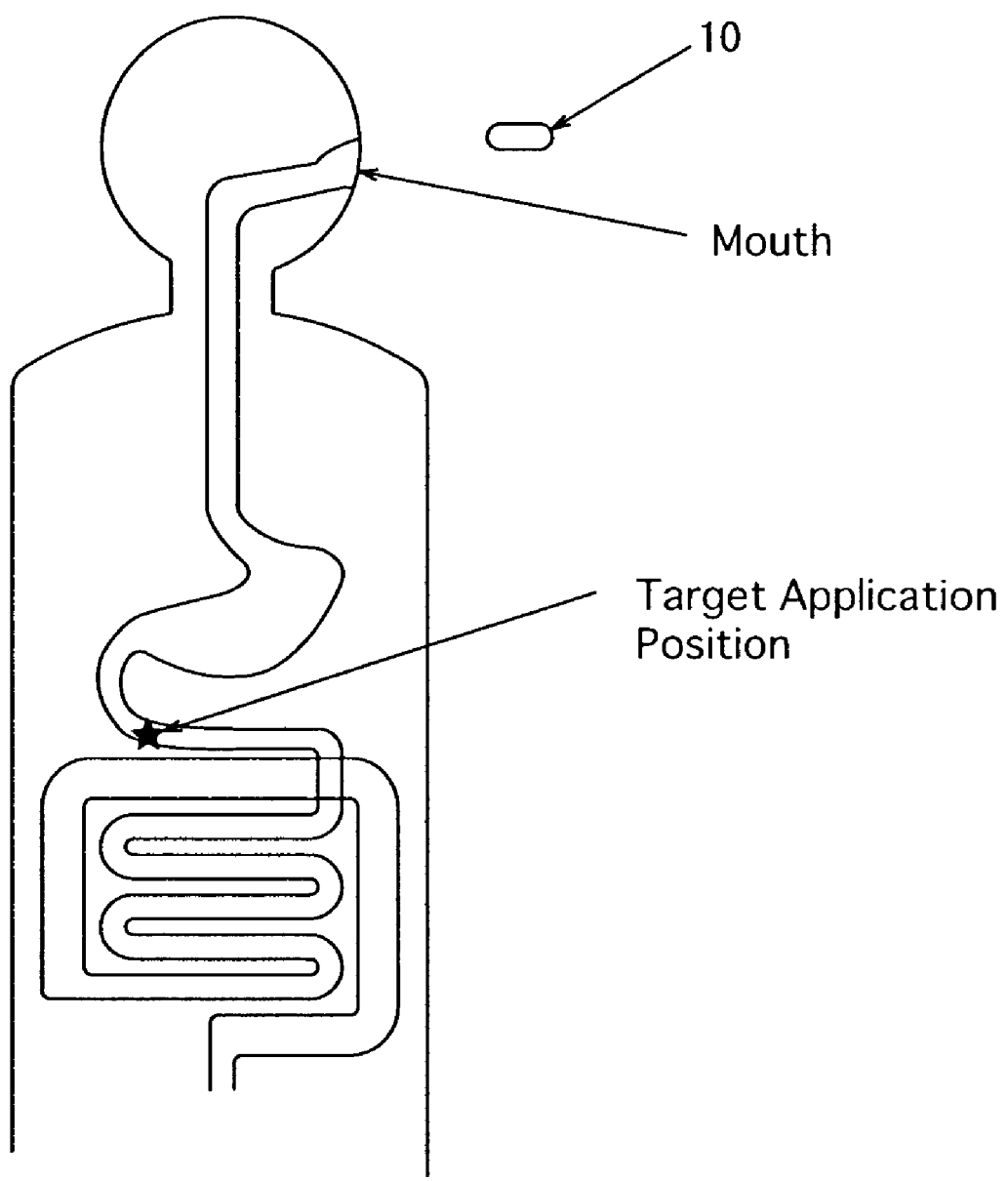
FIG. 22 is a view showing a human body for illustrating the conditions of use of a capsule endoscope.

After the capsule endoscope 10 is guided to the target position, the user pulls the flange lever 165 to release the connection between the engagement holder 151 and the capsule endoscope 10. Namely, when the flange lever 165 is pulled, the driving plate 155 moves to project from the forceps pipe 153 so that the connecting plates 158a to 158d change an elongated form. At the same time, since a distance between the shaft 159b and the shaft 159d is reduced, the base of the enlarged hole 12b is pressed by portions (the distal end of the driving plate 155) of the connecting plates 158b and 158c, which are connected by the shaft 159c. In this manner, the engagement holder 151 is pulled out of the enlarged hole 12b while pushing the capsule endoscope 10. As a result of this action, the capsule endoscope 10 is left at the target position of the patient (FIG. 22). Subsequently, after the capsule endoscope 10 is advanced in an excreting direction by peristalsis of the intestines while transmitting a video signal of images captured by the CMOS image sensor 13. The capsule endoscope 10 is ultimately excreted from the patient's body.

As described above, according to the embodiments of the present invention, the capsule endoscope 10 can be easily and reliably connected to the engagement holder 151 of the capsule connection forceps 150, and the capsule endoscope 10 can be easily and reliably guided to a target position while being held at the tip of the scope 101. Moreover, after the capsule endoscope 10 is guided to the target position, mere manipulation of the handle 163 of the capsule connection forceps 150 allows the connection with the capsule endoscope 10 to easily and reliably release so as to leave the capsule endoscope 10 at the target position.

Although the present invention has been applied to the electronic scope corresponding to a type of endoscope in the illustrated embodiments, the present invention is not limited to the endoscope. The present invention is also applicable to a member, insertable into the patient's body, having an elongated flexible portion that can be freely manipulated in a curved manner from one end thereof. Such a member can have a smaller width than that of the endoscope.

A fourth embodiment of the capsule endoscope guidance system will be described with reference to FIGS. 13 to 21. Basic structures of a capsule endoscope, an electronic endoscope, and a processor section for endoscope in the following illustrated embodiment are the same as those of the capsule endoscope 10, the scope section 100, and the endoscope processor section 200, which have been already described based on FIGS. 1 to 6. Furthermore, since a structure of a capsule endoscope holder is the same as that of the capsule endoscope holder shown in FIGS. 7 to 12, the same components and the components having the same functions as those of the capsule endoscope holder shown in FIGS. 7 to 12 are denoted by the same reference numerals, therefore the descriptions thereof are omitted.

Figure 3:
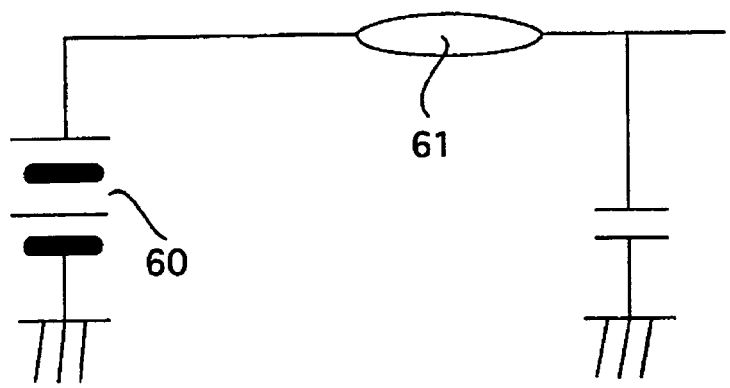
FIG. 3 is a block diagram showing a structure of a second embodiment of the capsule endoscope guidance system to which the present invention is applied.
Figure 13:
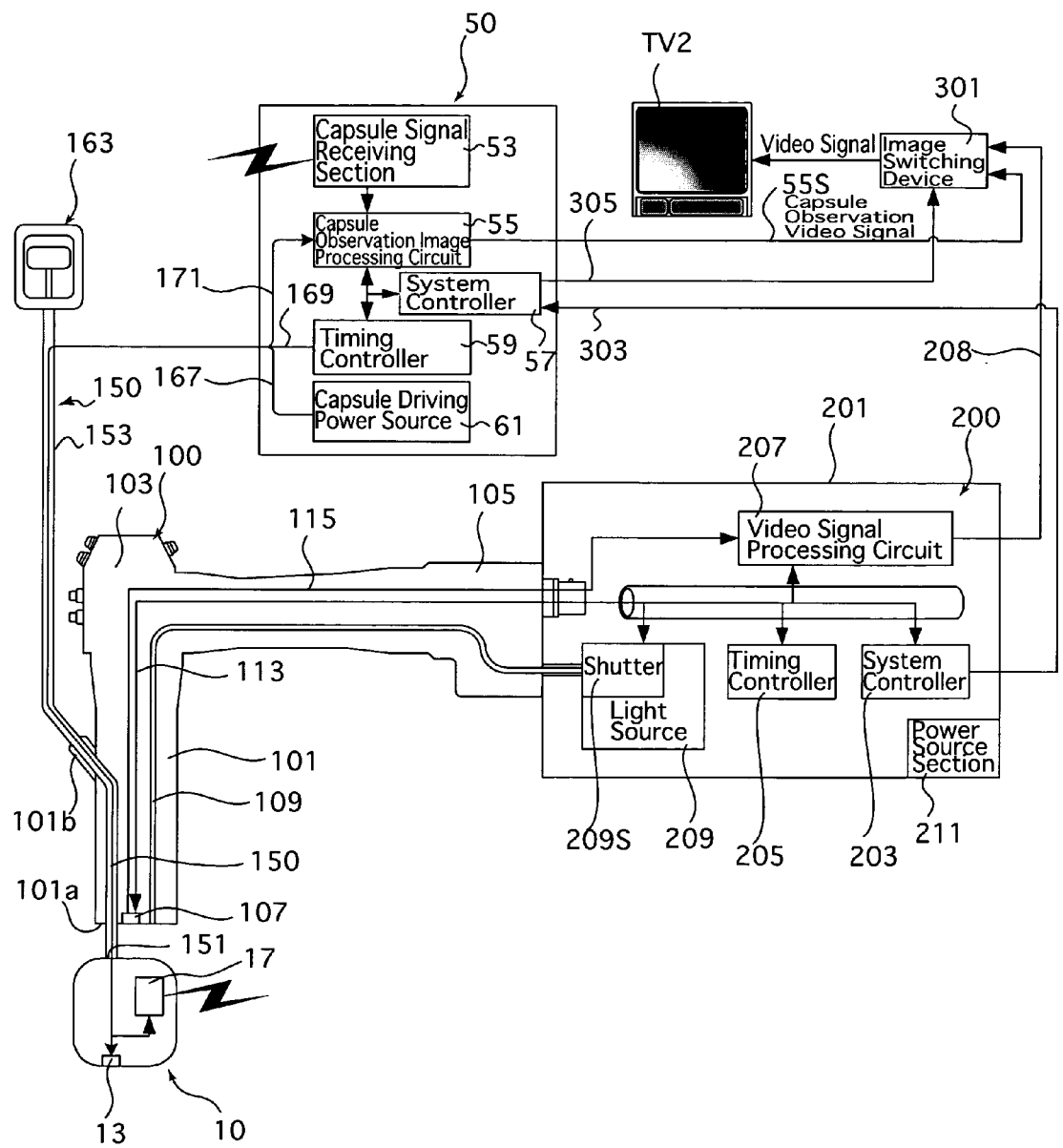
FIG. 13 is a schematic diagram showing a principal portion of a fourth embodiment of the capsule endoscope guidance system including a capsule endoscope having external terminals and a capsule endoscope holder for the capsule endoscope.

As shown in FIG. 13, a structure of the capsule-observation processor 50 is the same as that of the capsule-observation processor 50 shown in FIG. 3. In this embodiment, an image pickup device driving signal output from the timing controller 59 is transmitted via the image pickup device driving signal line 169 to the engagement holder 151. Capsule driving electric power output from the capsule driving power source 61 is transferred via the driving power source line 167 to the engagement holder 151. A video signal of images captured by the CMOS image sensor 13 of the capsule endoscope 10 is input via a video signal line 171 to the capsule observation image processing circuit 55.

Figure 14:
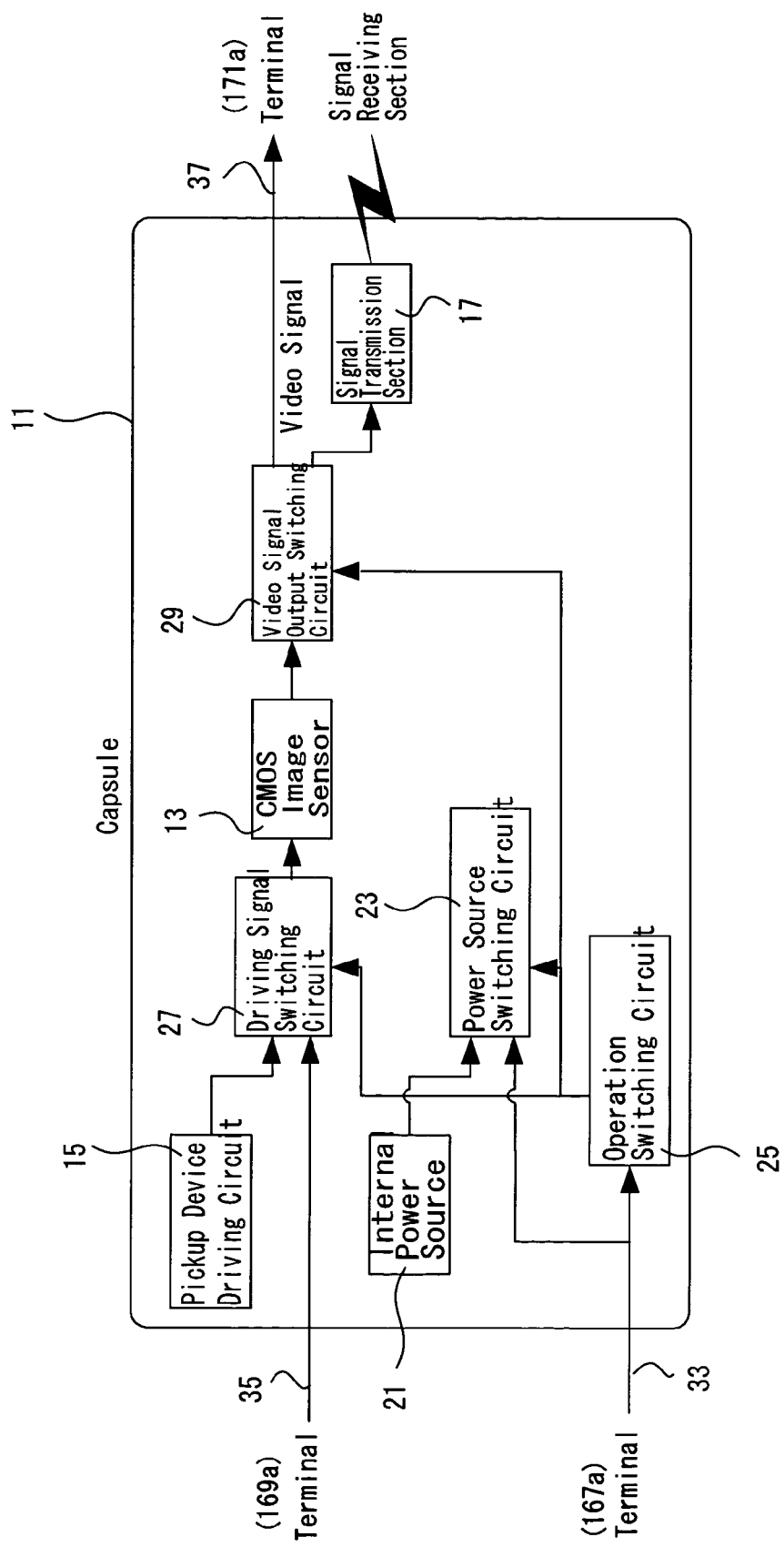
FIG. 14 is a block diagram showing a principal portion of another embodiment of a capsule endoscope.

The basic structure of the embodiment of the capsule endoscope 10 shown in FIG. 14 is the same as that of the capsule endoscope 10 shown in FIG. 4.

The power source switching circuit 23 switches an operational power source of the built-in circuits between the internal power source 21 and an external power source. In cooperation with the power source switching circuit 23, the operation switching circuit 25 switches an operation mode of the built-in circuits between the internal power source mode and the external power source mode.

The internal power source mode is also a normal operation mode of the capsule endoscope 10, which has been already described.

The external power source mode is a mode in which the capsule endoscope 10 operates in response to supply of driving electric power (external power source) via an external power source input terminal 33. For example, when external electric power is input from the driving electric power line 167a via the external power source input terminal 33 to the power source switching circuit 23 and the operation switching circuit 25, the operation switching circuit 25 switches its operation from the internal power source operation to the external power source operation. Subsequently, the power source switching circuit 23 switches OFF the internal power source 21 so as to operate in the external power source mode for supplying the external electric power to each of the included members and circuits.

Furthermore, the image pickup device driving signal switching circuit 27 is switched to perform an external image pickup device driving signal operation so that an image pickup device driving signal is input from the image pickup device driving signal line 169a via an external driving signal input terminal 35 to the CMOS image sensor 13. As a result, the CMOS image sensor 13 performs an image pickup operation. A video signal from the CMOS image sensor 13 is output from an external video signal output terminal 37 via the video signal output switching circuit 29 to the external video signal line 171a (capsule observation image processing circuit). In other words, the external power source mode is an operation mode in which the capsule endoscope 10 is connected and held by the capsule connection forceps 150.

A basic structure of the capsule connection forceps 150 used in this embodiment is the same as that shown in FIGS. 7 to 12.

Figure 15:
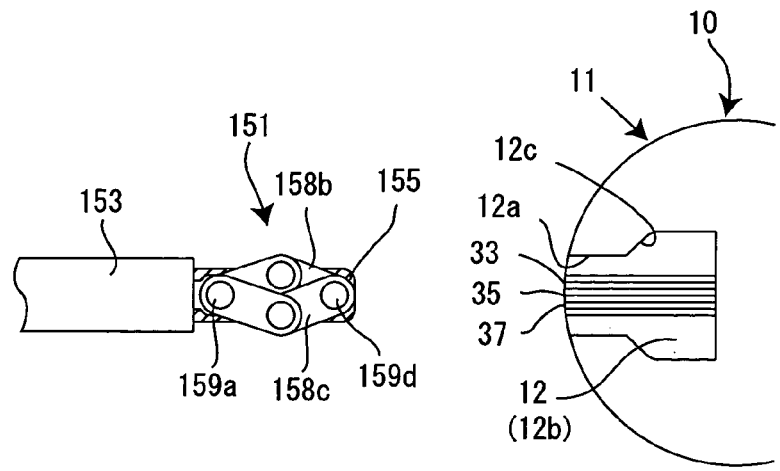
FIG. 15 is a view showing a state before the capsule endoscope is connected to the capsule endoscope holder.

The engagement hole 12 is formed in the sealed capsule container 11 of the capsule endoscope 10 (see FIG. 15). The engagement hole 12 has the narrowed opening 12a and the enlarged hole 12b that increases in diameter from the opening 12a toward the base thereof. The inclined face 12c extending from the opening 12a toward the base of the engagement hole 12 is formed between the opening 12a and the enlarged hole 12b. The engagement hole 12 in this embodiment is formed so that the opening 12a is sealed by the edge of the opening 12a and the outer circumferential face of the forceps pipe 153 in close contact with each other when the forceps pipe 153 is insertable and is being inserted into the opening 12a. Namely, the forceps pipe 153 is formed so as to serve as a sealing plug of the opening 12a.

On the inner face of the enlarged hole 12b of the engagement hole 12 (on the outer face with respect to the sealed capsule container 11), the external power source input terminal 33, the external driving signal input terminal 35 and the external video signal output terminal 37 are provided in an exposed state as external terminals. The external power source input terminal 33, the external driving signal input terminal 35 and the external video signal output terminal 37 extend in the same direction as that of pulling/inserting direction of the engagement holder 151 from the engagement hole 12, and the external power source input terminal 33, the external driving signal input terminal 35 and the external video signal output terminal 37 are arranged in a direction orthogonal to this direction at predetermined intervals.

Furthermore, the external power source input terminal 33, the external driving signal input terminal 35 and the external video signal output terminal 37 are connected via a water-proof switch 31 to the respective circuits in the sealed capsule container 11 (see FIGS. 20A through 21B). The water-proof switch 31 includes, as an operational portion, a normally open terminal within a water-proof cover exposed at the base of the enlarged hole 12b. In other words, the external power source input terminal 33, the external driving signal input terminal 35 and the external video signal output terminal 37 and the respective circuits in the sealed capsule container 11 are normally in an isolated state.

Figure 20A:
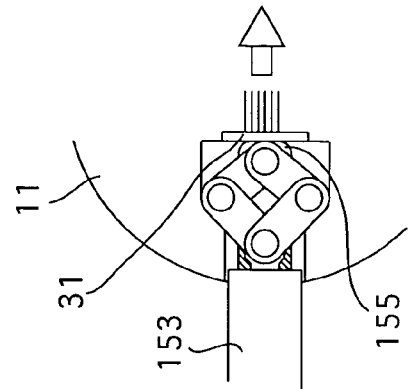
FIG. 20A is a view showing an embodiment of the capsule endoscope before its attachment to the capsule endoscope holder.
Figure 20B:
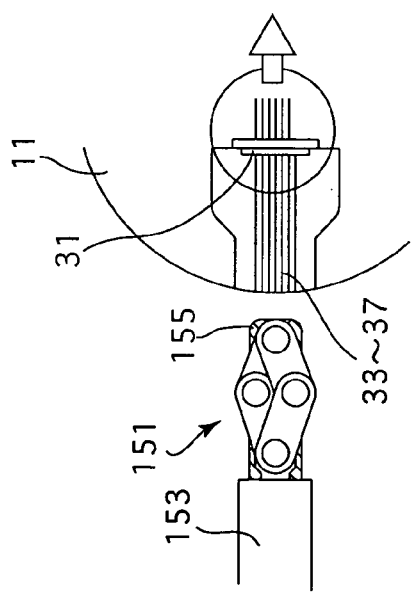
FIG. 20B is a view showing the embodiment of the capsule endoscope after its attachment.

When the engagement holder 151 is inserted into the engagement hole 12, the water-proof switch 31 is pressed by the end of the driving plate 155. Furthermore, the connecting plates 158a to 158d open outwards so that the engagement holder 151 is connected into the engagement hole 12 so as not to come off from the engagement hole 12. In such a state, the water-proof switch 31 is pressed strong enough to be switched ON (FIG. 20B). This ON state is maintained while the engagement holder 151 is engaged with the engagement hole 12.

Figure 16:
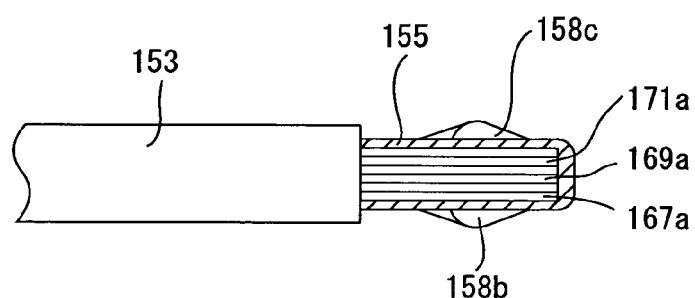
FIG. 16 is a view showing a back face of an engaging portion of the capsule endoscope holder.
Figure 17:
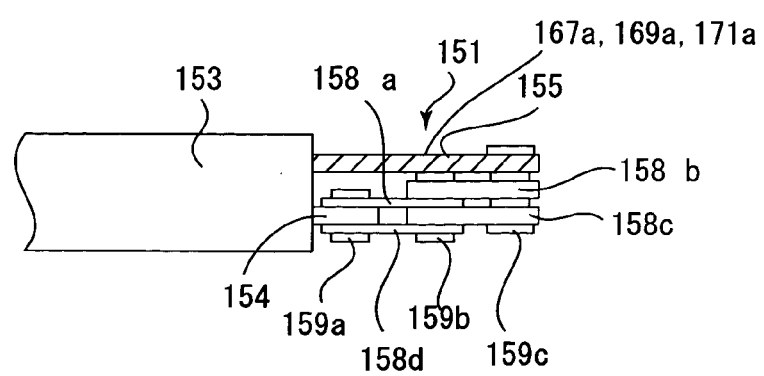
FIG. 17 is a view showing a top face of the engaging portion of the capsule endoscope holder.

As shown in FIG. 16, terminals 167a, 169a, and 171a, which extend in a longitudinal direction, are provided on one face of the driving plate 155 of the engagement holder 151, whose face is opposite to the face where the shafts 159a to 159d are attached. The terminals 167a, 169a, and 171a are respectively connected to the lines 167, 169, and 171. The terminals 167a, 169a, and 171a are brought into a sliding contact with the corresponding external power source input terminal 33, the external driving signal input terminal 35 and the external video signal output terminal 37, respectively, when the engagement holder 151 is inserted into the engagement holder 12 for connection. In this manner, the terminals 167a, 169a, and 171a maintain an electrically conductive state when connected.

This capsule endoscope connection mechanism is used in the following manner. The engagement holder 151 is inserted through the forceps insertion port 111b into the scope section 100 connected to the endoscope processor section 200 so as to project from the forceps port 111a. At this time, the flange lever 165 is pulled so as to bring the engagement holder 151 into a closed (reduced in width) state (FIGS. 5, 15, and 20A).

Figure 18:
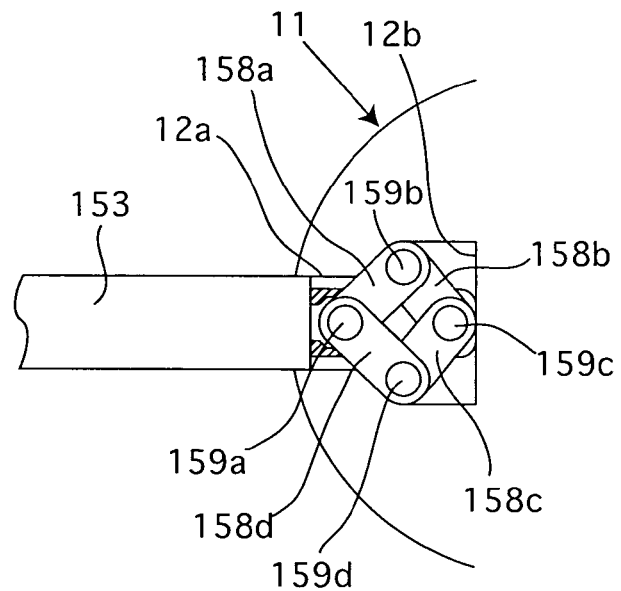
FIG. 18 is a view showing a principal portion in a state where the capsule endoscope is engaged with the engaging portion of the capsule endoscope holder.
Figure 19:
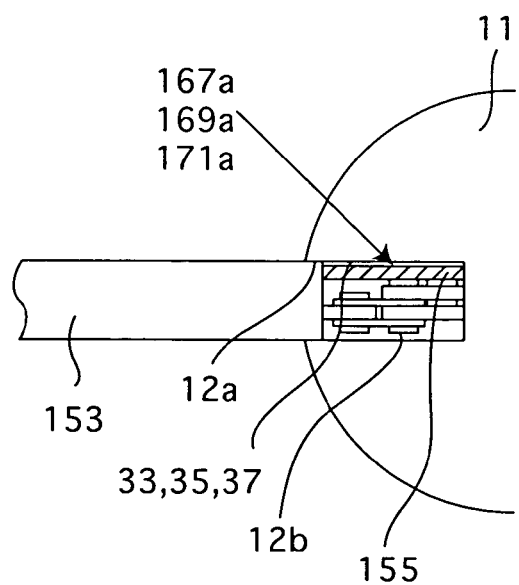
FIG. 19 is a plan view showing a principal portion in a state where the capsule endoscope is engaged with the engaging portion of the capsule endoscope holder.

The engagement holder 151 in a closed state is inserted into the engagement hole 12 of the capsule endoscope 10. Thereafter, the force for holding the handle 163 is released while the end of the engagement holder 151 is inserted into the engagement hole 12 so as to abut against the base of the engagement hole 12, thereby opening (increasing in width) the engagement holder 151 by the biasing force of the spring 162 (FIGS. 18 and 20B). Namely, since the driving plate 155 moves so as to be drawn back into the forceps pipe 153, the distance between the connecting shafts 159b and 159d is increased to widely open the connecting plates 158a and 158d, pressing the boundary inclined face 12c between the opening 12a and the enlarged hole 12b. As a result, the end of the driving plate 155 is pressed against the water-proof switch 31 attached to the bottom of the enlarged hole 12b, and the engagement holder 151 is prevented from being pulled out of the opening 12a. Due to a opening action of the engagement holder 151, the connecting plates 158a to 158d are opened inside within the enlarged hole 12b to be larger than the diameter of the opening 12a, thereby providing a connected state for preventing the connecting plates 158a to 158d from being pulled out of the opening 12a. At the same time, a clattering movement is prevented by the force of the connecting plates 158a and 158d and the driving plate 155 for pushing the inclined face 12c and the bottom of the enlarged hole 12b. In addition, the capsule endoscope 10 is connected and held at the distal end of the scope 101 that is inserted into the patient's body while the water-proof switch 31 is in an ON state. The tip of the forceps pipe 153 is fitted into the opening 12a in a liquid-proof state, thereby sealing the enlarged hole 12b.

Since the opening 12a is sealed by the forceps pipe 153 as described above, there is no possibility of trouble occurring due to electrical leakage or the like.

Figure 21A:
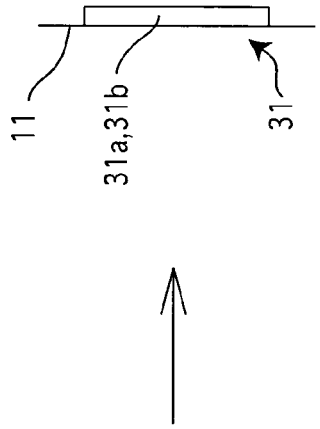
FIGS. 21A and 21B are views respectively showing ON and OFF states of a water-proof switch of another embodiment of the capsule endoscope.
Figure 21B:
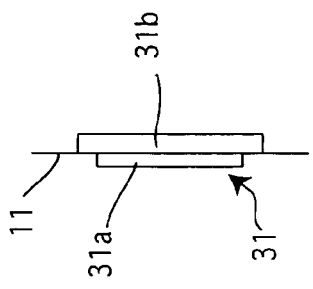

The water-proof switch 31 includes a stretchable operational portion 31a exposed in the enlarged hole 12b, and a contact portion 31b positioned within the capsule. The operational portion 31a prevents water from entering the capsule. An OFF state of the water-proof switch 31 is shown in FIGS. 20A and 21A, whereas an ON state thereof is shown in FIGS. 20B and 21B.

The terminals 167a, 169a, and 171a of the driving plate 155 are electrically conductive with the external power source input terminal 33, the external driving signal input terminal 35 and the external video signal output terminal 37, respectively, so that the capsule endoscope 10 can be switched to perform its operation in the external power source mode. Namely, in response to supply of driving electric power (external power source) via the driving power source line 167 and the terminal 167a and the external power source input terminal 33, the operation mode of the capsule endoscope 10 is switched to the external power source mode. In response to supply of an image pickup device driving signal via the image pickup device driving signal line 169 and the terminal 169a and the external driving signal input terminal 35, a video signal of images captured by the CMOS image sensor 13 is output to the capsule-observation processor 50 via the external video signal output terminal 37 and the terminal 171a, and the video signal line 171.

On the other hand, for the connected capsule connection forceps 150, the capsule-observation processor 50 supplies driving electric power from the capsule driving power source 61 to the driving power source line 167 while supplying an image pickup device driving signal from the timing controller 59 to the image pickup device driving signal line 169. Subsequently, a video signal is input from the video signal line 171 to the capsule observation image processing circuit 55, from which the video signal is output as a capsule observation video signal 55S. The capsule observation video signal 55S passes through the image switching device 301 to be displayed as an image on the screen of the monitor television TV2.

In this connected state, the user inserts the capsule endoscope 10 through the patient's mouth. The user manipulates the scope 101 to guide the capsule endoscope to a target position while viewing the images on the screen of the monitor television.

After the capsule endoscope 10 is guided to the target position, the user pulls the flange lever 165 to release the connection between the engagement holder 151 and the capsule endoscope 10. Namely, when the flange lever 165 is pulled, the driving plate 155 moves so as to project from the forceps pipe 153, so that the connecting plates 158a to 158d changes to an elongated form whereby the distance between the shafts 159a and 159b is reduced. Thereafter, the engagement holder 151 is pulled out of the enlarged hole 12b while pressing the bottom of the enlarged hole 12b with the connected portions of the connecting plates 158b and 158c through the shaft (the tip of the driving plate 155) to push the capsule endoscope 10. Subsequently, the capsule endoscope 10 is left at the target position of a patient (FIG. 22).

Thereafter, the driving plate 155 is separated from the water-proof switch 31, and the external power source input terminal 33, the external driving signal input terminal 35 and the external video signal output terminal 37 are isolated from the respective circuits in the capsule container 11. As a result, the external power source is replaced by the internal power source 21 so that the operation switching circuit 25 switches its operation mode to the internal power source operation mode to start the original capsule endoscope operation. Since the external power source input terminal 33, the external driving signal input terminal 35 and the external video signal output terminal 37 are isolated from the circuits in the capsule container 11 after the capsule endoscope 10 is left at the target position in the above-described manner, electrical leakage does not occur therein.

Thereafter, the capsule endoscope 10 is carried in an excreting direction by peristalsis of the intestines while transmitting a video signal of images captured by the CMOS image sensor 13. The capsule endoscope 10 is ultimately excreted from the patient's body.

As described above, according to the embodiments of the present invention, the capsule endoscope 10 is held by the engagement holder 151 of the capsule connection forceps 150. At the same time, the external power source input terminal 33, the external driving signal input terminal 35 and the external video signal output terminal 37 can be easily and reliably connected to the terminals 167a, 169a, and 171a, respectively. Therefore, the capsule endoscope 10 is held at the distal end of the scope 101 so as to easily and reliably guide the capsule endoscope 10 to a target position while electric power is being supplied to the capsule endoscope 10. In addition, after the capsule endoscope 10 is guided to the target position, mere manipulation of the handle 163 of the capsule endoscope forceps 150 allows the connection with the capsule endoscope 10 to be released in an easy and reliable manner so as to leave the capsule endoscope 10 to the target position.

Although the present invention is applied to the electronic scope which is one type of endoscope in the illustrated embodiment, the present invention is not limited thereto, and can be applied to a member insertable into the patient's body, which has an elongated flexible portion allowing free manipulation in a curved manner from one end thereof. In such a case, this member would be electrically conductive with the external power source input terminal 33, the external driving signal input terminal 35 and the external video signal output terminal 37 of the capsule endoscope so as to be capable of giving and receiving electric power and signals. Such a member is desirable because it can have a smaller diameter than that of the endoscope.

Although the external power source input terminal 33, the external driving signal input terminal 35, and the external video signal output terminal 37 are shown as external terminals of the capsule endoscope 10 in the illustrated embodiment, the external terminals are not limited thereto.

Moreover, the external terminals of the capsule endoscope 10 can be provided on the bottom of the engagement hole, and the terminal on the engagement holder 151 side may alternatively be provided on the tip end face of the driving plate 155.

Although the engagement holder 151 is constructed from four connecting plates 158a to 158d connected in a circular manner by overlapping their ends to form a quadrangle so as to constitute a thin quadric crank chain mechanism with the shafts 159a through 159d orthogonally crossing the faces of the connecting plates, the present invention is not limited thereto. For example, the connecting plates 158a to 158d can be connected with each other in a circular manner so that their shorter sides are opposed to each other to form a thick quadric crank chain mechanism by shafts extending along the shorter sides. Alternatively, the connecting plates can be bar-like members instead of being the plate-like members.

Although lengths of the connecting plates 158a to 158d (distances between the shafts) are identical with each other in the illustrated embodiment, the lengths may be varied. Moreover, if the connecting plates 158a and 158d are shorter than the connecting plates 158b and 158c, or moving shafts 159b and 159d are provided in the middle of the connecting plates 158a and 158d to reduce the length between the fixed shaft 159a and the moving shaft 159b, and that of between the fixed shaft 159a and the moving shaft 159d, the degree of opening and closing between the connecting plates 158a and 158d (a rate of change in narrow angle) in response to a stroke of the driving plate 155 is increased.

The quadric crank chain mechanism applied to the structure of the engagement holder 151 in the illustrated embodiment is not limited thereto. Any structure of the engagement holder 151 is applicable as long as the engagement holder 151 is insertable into and removable from the engagement hole of the capsule endoscope so as to be opened out within the inserted state to connect and hold the capsule endoscope; for example, a balloon-like structure is applicable.

As is apparent from the above description, the capsule endoscope can be guided to a desired target application-position with the endoscope. As a result, a user can quickly guide and leave the capsule endoscope at a position to which the user wishes to use the capsule endoscope, or the vicinity thereof.

By providing power source supply device and image pickup device driving signal output device for the capsule endoscope holding device, it is not necessary to use an internal power source of the capsule endoscope while the capsule endoscope is being held by the capsule endoscope holding device. Moreover, if the capsule endoscope holding device is equipped with the video signal transmission device as described above, a video signal of images captured by the image pickup device included in the capsule endoscope can be output to, for example, an external monitor television to be displayed thereon. Thus, the capsule endoscope can be more precisely guided to a target position.

By providing an engagement hole for the capsule container of the capsule endoscope and providing electrically conductive terminals with an electric wiring in the capsule as well as with terminals of the engagement member inserted into the engagement holder, it is possible to supply electric power to the capsule endoscope to allow the communication therewith.

Moreover, the capsule endoscope can be held at the tip of the endoscope, which is inserted in the patient's body. At the same time, a power source and a driving pulse can be supplied so that a video signal of images captured by a camera included in the capsule endoscope is output to external equipment.

Obvious changes may be made in the specific embodiments of the present invention described herein, such modifications being within the spirit and scope of the invention claimed. It is indicated that all matter contained herein is illustrative and does not limit the scope of the present invention.

What is claimed is:

1. A capsule endoscope guidance system including a member having an elongated flexible portion which can be guided to a desired position in a body cavity of a patient's body by manipulating a distal end portion of said member wherein the elongated flexible portion bends in accordance with an operation at a proximal end portion of said member, comprising:
    a capsule endoscope holding device, provided at a distal end of said elongated flexible portion, for removably holding a capsule endoscope, said capsule endoscope holding device equipped with a power source supply device for supplying electric power to the capsule endoscope while holding the capsule endoscope; and
    a removal/attachment manipulation device provided on the proximal end portion, for manipulating removal and attachment of the capsule endoscope holding device;
    wherein the capsule endoscope comprises, in a water-resistant sealed capsule container:
    an image pickup device;
    a driving signal output device for outputting a driving signal for driving the image pickup device;
    an illumination device for illuminating an object image is to be captured by said image pickup device;
    a transmission device for wirelessly transmitting a video signal, captured and output by the image pickup device, outside said water-proof sealed capsule container; and
    a power source for supplying electric power to said image pickup device, said driving signal output device, said illumination device, and said transmission device.

2. A capsule endoscope guidance system including a member having an elongated flexible portion which can be guided to a desired position in a body cavity of a patient's body by manipulating a distal end portion of said member wherein the elongated flexible portion bends in accordance with an operation at a proximal end portion of said member, comprising:
    a capsule endoscope holding device, provided at a distal end of said elongated flexible portion, for removably holding a capsule endoscope, said capsule holding device equipped with an image pickup device driving signal output device for supplying an image pickup device driving signal to the capsule endoscope while holding the capsule endoscope; and
    a removal/attachment manipulation device provided on the proximal end portion, for manipulating removal and attachment of the capsule endoscope holding device;
    wherein the capsule endoscope comprises, in a water-resistant sealed capsule container:
    an image pickup device;
    a driving signal output device for outputting a driving signal for driving the image pickup device;
    an illumination device for illuminating an object image is to be captured by said image pickup device;
    a transmission device for wirelessly transmitting a video signal, captured and output by the image pickup device, outside said water-proof sealed capsule container; and
    a power source for supplying electric power to said image pickup device, said driving signal output device, said illumination device, and said transmission device.

3. The capsule endoscope guidance system according to claim 2, wherein the capsule endoscope holding device is equipped with a video signal transmission device for receiving transmission of a video signal output from the capsule endoscope while holding the capsule endoscope.

4. The capsule endoscope guidance system according to claim 1, wherein the capsule endoscope further includes a switching device for switching to an operation powered by an external power source supplied from the power source supply device while said capsule endoscope is held by the capsule endoscope holding device.

5. The capsule endoscope guidance system according to claim 2, wherein the capsule endoscope further includes a switching device for switching a driving mode of the included image pickup device driven by an image pickup device driving signal, input from the capsule endoscope holding device, while said capsule endoscope is held by the capsule endoscope holding device.

6. The capsule endoscope guidance system according to claim 1, wherein said capsule endoscope further comprises:
    a detection device for detecting that the capsule endoscope is held by the capsule endoscope holding device; and
    a switching device for switching to an operation powered by an external power source supplied from the power source supply device when the detection device detects that the capsule endoscope is held by the capsule endoscope holding device.

7. The capsule endoscope guidance system according to claim 2, wherein the capsule endoscope comprises:
    a detection device for detecting that the capsule endoscope is held by the capsule endoscope holding device; and
    a switching device for switching an image pickup device driving signal for driving the included image pickup device driven by an image pickup device driving signal input from the capsule endoscope holding device when the detection device detects that the capsule endoscope is held by the capsule endoscope holding device.

8. A capsule endoscope holder for holding a capsule endoscope including an engagement hole having a narrow opening formed in a sealed capsule container, comprising:
    a member having an elongated flexible portion which can bend in accordance with an operation at a proximal end of said member, the distal end of said flexible portion being inserted into said sealed capsule container, which is insertable into a patient's body, so that said sealed capsule container projects from the distal end of the flexible portion; and
    an openable/closeable engagement member provided at the distal end of said elongated flexible portion,
    wherein said openable/closeable engagement member is inserted into the engagement hole in a closed state, is opened outwards inside said engagement hole to be engaged in the engagement hole so as not to be pulled out of the engagement hole; and
    wherein said openable/closeable engagement member is closed in order to be pulled out of the engagement hole.

9. The capsule endoscope holder according to claim 8, wherein said member of said capsule endoscope holder is provided with a flexible pipe;
    wherein said openable/closeable engagement member includes a movement manipulation member provided at the proximal end of said flexible pipe and a cable driven by the movement manipulation member, the movement manipulation member and the cable being slidably inserted into said flexible pipe; and wherein said openable/closeable engagement member is attached to the distal end of said flexible pipe, said openable/closable engagement member being closed and opened by relative movement between said cable and said flexible pipe.

10. The capsule endoscope holder according to claim 8, wherein said sealed capsule container, which is insertable into the patient's body, comprises an endoscope.

11. The capsule endoscope holder according to claim 9, wherein said openable/closable engagement member comprises:

four connecting members; and a plate-like member driven by a cable so as to project from and be drawn back into said flexible pipe;

wherein said four connecting members constitute a quadric crank chain by a fixed shaft attached to the distal end of said flexible pipe and a driving shaft attached to said plate-like member, said fixed shaft and said driving shaft being relatively moveable to be away from each other and to approach each other; and wherein said fixed shaft and said driving shaft move away from each other and approach each other in a direction orthogonal to a moving direction of said plate-like member via movement of said plate-like member in projecting and drawing directions with respect to said flexible pipe.

12. The capsule endoscope holder according to claim 11, wherein when said openable/closable engaging member is inserted into said engagement hole, said plate-like member projects forwards from the distal end of said flexible pipe, and thereafter said plate-like member is relatively moved in a drawing direction with respect to said flexible pipe; and wherein two connecting members, of said four connecting members, which are supported by said fixed shaft abut against a circumferential edge of an opening of said engagement hole while being opened in a direction wherein said fixed shaft and said driving shaft approach each other to draw said flexible pipe into said engagement hole to thereby close the opening with said flexible pipe to obtain a connected state.

13. The capsule endoscope holder according to claim 12, wherein, when said plate-like member relatively moves with respect to said flexible pipe in a projecting direction in said connected state, said two connecting members supported by said fixed shaft are closed so that said fixed shaft and said driving shaft move away from each other while the distal end of the plate-like member presses a base of said engagement hole to, thereby disconnect said flexible pipe from said engagement hole.

14. The capsule endoscope holder according to claim 11, wherein one of said cable and said plate-like member is biased by a spring member in a direction wherein said openable/closeable engagement member is opened.

15. A capsule endoscope comprising:

an engagement hole having closed end, formed in a sealed capsule container of the capsule endoscope; and external terminals provided in the engagement hole, said external terminals being electrically conductive with an electrical wiring in the sealed capsule container, and said external terminals being electrically conductive with terminals of an engagement member inserted into the engagement hole.

16. The capsule endoscope according to claim 15, wherein said engagement hole comprises a narrowed opening, and said engagement hole is enlarged toward the base.

17. The capsule endoscope according to claim 16, wherein said engagement member comprises an elongated flexible portion which can bend in accordance with an operation at a proximal end thereof, wherein the distal end of said elongated flexible portion is inserted into the proximal end of a member which is insertable into a patient's body so that said distal end of said elongated flexible portion inserted into a patient's body is held by engagement between said engagement member and said engagement hole.

18. The capsule endoscope according to claim 15, wherein a switching device for starting and stopping electrical conduction between said external terminals and the electric wiring in the capsule container is provided in the engagement hole;

wherein an operational portion of the switching device is provided at the base of said engagement hole; and wherein said switching device allows electrical conduction between the external terminals and the electric wiring in the capsule container while the engagement member is inserted into the engagement hole so as to activate said operational portion.

19. A capsule endoscope holder for holding a capsule endoscope including an engagement hole with a narrow opening, formed on an end of a capsule; and external terminals provided in the engagement hole, being electrically conductive with an electrical wiring in the capsule container, said capsule endoscope holder comprising:

an engagement member provided at a distal end of a flexible long member, said engagement member being inserted into the engagement hole in a closed state, said engagement member engaging with the engagement hole when said engagement member is opened within the engagement hole, whereas said engagement member is disengaged with the engagement hole when the engagement member is closed, wherein the engagement member further includes terminals being electrically conductive with the corresponding external terminals in the engagement hole while the engagement member is inserted in the engagement hole.

20. The capsule endoscope holder according to claim 19, wherein the capsule endoscope holder includes said flexible long member having an elongated flexible portion which can bend in accordance with an operation at a proximal end thereof, wherein the distal end of said elongated flexible portion of said flexible long member is inserted into the proximal end of a member which is insertable into a patient's body; wherein said engagement member being provided at the distal end of said elongated flexible portion of said flexible long member; and wherein the engagement member is inserted into the engagement hole in a closed state to be opened within the engagement hole so as to engage with the engagement hole, and in order to disengage said engagement member, said engagement is closed so as to be drawn out of said engagement hole.

21. The capsule endoscope holder according to claim 19, wherein said flexible long member comprises a flexible pipe;

wherein said engagement member includes a movement manipulation member provided at the proximal end of said flexible pipe and a cable driven by said movement manipulation member, said movement manipulation member and said cable being slidably inserted into said flexible pipe; and said engagement member is attached to the distal end of said flexible pipe, wherein said engagement member is closed and opened with relative movement between said cable and said flexible pipe.

22. The capsule endoscope holder according to claim 21, wherein said openable/closable engagement member comprises:
four connecting members; and
a plate-like member driven by a cable so as to project from and be drawn back into said flexible pipe;
wherein said four connecting members constitute a quadric crank chain by a fixed shaft attached to the distal end of said flexible pipe and a driving shaft attached to said plate-like member, said fixed shaft and said driving shaft being relatively moveable to be away from each other and to approach each other; and
wherein said fixed shaft and said driving shaft move away from each other and approach each other in the same direction as said plate-like member moves along via movement of said plate-like member in projecting and drawing directions with respect to said flexible pipe.

23. The capsule endoscope holder according to claim 22, wherein the terminals of the engagement member are provided at predetermined intervals on a face of the plate-like member, opposite to a face where the fixed shaft is attached and the connecting members are positioned in a direction approximately orthogonal to a direction in which the plate-like member is inserted into and drawn out of the engagement hole, and
wherein the external terminals of the capsule endoscope are provided on a surface of the engagement hole so as to correspond to the terminals of the plate-like member.

24. The capsule endoscope holder according to claim 23, wherein when said openable/closable engaging member is inserted into said engagement hole, said plate-like member projects forwards from the distal end of said flexible pipe, and thereafter said plate-like member is relatively moved in a drawing direction with respect to said flexible pipe; and
wherein two connecting members, of said four connecting members, which are supported by said fixed shaft abut against a circumferential edge of an opening of said engagement hole while being opened in a direction wherein said fixed shaft and said driving shaft approach each other to draw said flexible pipe into said engagement hole to thereby close the opening with said flexible pipe to obtain a connected state, whereby each of the terminals attached to the plate-like member is brought into an electrically conductive state with each of the external terminals provided in the engagement hole.

25. The capsule endoscope holder according to claim 24, wherein, when the plate-like member relatively moves with respect to said flexible pipe in a projecting direction in the connected state, the two connecting members supported by the fixed shaft are closed in a direction wherein said fixed shaft and said driving shaft move away from each other while the distal end of the plate-like member presses the base of the engagement hole, so that the terminals attached to the plate-like member are not electrically connected with the respective external terminals provided in the engagement hole, thereby separating the flexible pipe from the engagement hole.

26. The capsule endoscope holder according to claim 24, wherein an operational portion of a normally open switch device for starting and stopping electrical conduction between each of the external terminals provided in the engagement hole and an electronic member included in the capsule is provided at the base of the engagement hole, wherein the operational portion is pressed by the plate-like member in said connected state to be closed when the plate-like member is inserted into the engagement hole.

27. The capsule endoscope holder according to claim 24, wherein the external terminals are connected to a power source provided within the capsule container so that electric power is supplied from the terminals.

28. The capsule endoscope holder according to claim 24, wherein the external terminals are connected to a driving signal switching circuit for driving an image pickup device provided within the capsule container so that an image pickup device driving signal is supplied from the external terminals.

* * * * *